(12) United States Patent
Baroni et al.

(10) Patent No.: US 11,753,365 B2
(45) Date of Patent: Sep. 12, 2023

(54) METHODS OF TREATING FIBROSIS

(71) Applicant: Nogra Pharma Limited, Dublin (IE)

(72) Inventors: Sergio Baroni, Villa d'adda (IT);
Salvatore Bellinvia, Mendrisio (CH);
Francesca Viti, Mendrisio (CH)

(73) Assignee: Nogra Pharma Limited, Dublin (IE)

( * ) Notice: Subject to any disclaimer, the term of this patent is extended or adjusted under 35 U.S.C. 154(b) by 34 days.

(21) Appl. No.: 17/199,860

(22) Filed: Mar. 12, 2021

(65) Prior Publication Data

US 2022/0033346 A1 Feb. 3, 2022

Related U.S. Application Data

(60) Continuation of application No. 15/593,864, filed on May 12, 2017, now Pat. No. 11,046,641, which is a division of application No. 14/377,362, filed as application No. PCT/EP2013/052617 on Feb. 8, 2013, now Pat. No. 9,682,923.

(60) Provisional application No. 61/644,544, filed on May 9, 2012.

(30) Foreign Application Priority Data

Feb. 9, 2012 (EP) .................... 12425027

(51) Int. Cl.
| C07C 229/44 | (2006.01) |
| A61K 31/196 | (2006.01) |
| A61K 31/343 | (2006.01) |
| A61K 31/357 | (2006.01) |
| A61P 1/04 | (2006.01) |

(52) U.S. Cl.
CPC .......... *C07C 229/44* (2013.01); *A61K 31/196* (2013.01); *A61K 31/343* (2013.01); *A61K 31/357* (2013.01); *A61P 1/04* (2018.01)

(58) Field of Classification Search
None
See application file for complete search history.

(56) References Cited

U.S. PATENT DOCUMENTS

| 3,211,610 A | 10/1965 | Rogers |
| 3,444,232 A | 5/1969 | Bernstein |
| 4,036,951 A | 7/1977 | Halpern et al. |
| 4,348,223 A | 9/1982 | Grove |
| 4,404,215 A | 9/1983 | Vincent et al. |
| 4,429,152 A | 1/1984 | Gries et al. |
| 4,720,506 A | 1/1988 | Munakata et al. |
| 4,869,913 A | 9/1989 | Gries et al. |
| 4,933,330 A | 6/1990 | Jorgensen et al. |
| 5,262,549 A | 11/1993 | Telfer et al. |
| 5,302,751 A | 4/1994 | Manimaran et al. |
| 5,519,014 A | 5/1996 | Borody |
| 5,594,015 A | 1/1997 | Kurtz et al. |
| 5,594,151 A | 1/1997 | Stolowitz |
| 6,114,382 A | 9/2000 | Moretti |
| 6,194,627 B1 | 2/2001 | Geissler et al. |
| 6,326,364 B1 | 12/2001 | Lin et al. |
| 6,369,098 B1 | 4/2002 | Pershadsingh et al. |
| 6,403,656 B1 | 6/2002 | Rivier et al. |
| 6,583,128 B2 | 6/2003 | Ekwuribe et al. |
| 6,602,869 B1 | 8/2003 | Galey et al. |
| 6,844,003 B2 | 1/2005 | Galey et al. |
| 6,884,821 B1 | 4/2005 | Shinoda et al. |
| 6,903,082 B2 | 6/2005 | Ekwuribe et al. |
| 7,015,249 B1 | 3/2006 | Vanden Heuvel et al. |
| 7,049,342 B2 | 5/2006 | Miyachi et al. |
| 7,098,025 B1 | 8/2006 | Auwerx et al. |
| 7,176,204 B2 | 2/2007 | Miyachi et al. |
| 7,425,578 B2 | 9/2008 | Ekwuribe et al. |
| 7,429,676 B2 | 9/2008 | Weltering et al. |
| 7,749,980 B2 | 7/2010 | Plourde, Jr. et al. |
| 7,998,474 B2 | 8/2011 | Kelly |
| 8,030,520 B2 | 10/2011 | Sundermeier et al. |
| 8,138,357 B2 | 3/2012 | Naccari et al. |
| 8,153,693 B2 | 4/2012 | Baroni et al. |
| 8,153,841 B2 | 4/2012 | Naccari et al. |
| 8,420,698 B2 | 4/2013 | Lan-Hargest et al. |
| 8,450,506 B2 | 5/2013 | Naccari et al. |
| 8,492,438 B2 | 7/2013 | Chung et al. |
| 8,501,806 B2 | 8/2013 | Baroni et al. |
| 8,710,100 B2 | 4/2014 | Naccari et al. |
| 8,754,127 B2 | 6/2014 | Baroni et al. |
| 8,796,282 B2 | 8/2014 | Karnik |
| 8,796,334 B2 | 8/2014 | Baroni et al. |
| 9,133,099 B2 | 9/2015 | Naccari et al. |
| 9,345,680 B2 | 5/2016 | Naccari et al. |
| 9,511,041 B2 | 12/2016 | Baroni et al. |
| 9,561,202 B2 | 2/2017 | Naccari et al. |

(Continued)

FOREIGN PATENT DOCUMENTS

| CN | 101243039 A | 8/2008 |
| CN | 101878027 A | 11/2010 |

(Continued)

OTHER PUBLICATIONS

Yang et al (Inflamm Res 59:1061-1071, 2010) (Year: 2010).*
Declaration of Salvatore Bellinvia under 37 C.F.R. 1.132 submitted Nov. 9, 2020 in U.S. Appl. No. 15/593,864, now U.S. Pat. No. 11,046,641 (Year: 2020).*
U.S. Appl. No. 13/131,978, Methods for Preventing or Reducing Colon Carcinogenesis, filed Aug. 11, 2011, Abandoned.
U.S. Appl. No. 15/088,654, Methods for Preventing or Reducing Colon Carcinogenesis, filed Apr. 1, 2016, U.S. Pat. No. 9,913,817.
U.S. Appl. No. 13/201,786, Alkylamido Compounds and Uses Thereof, filed Nov. 17, 2011, U.S. Pat. No. 8,754,127.
U.S. Appl. No. 14/255,255, Alkylamido Compounds and Uses Thereof, filed Apr. 17, 2014, U.S. Pat. No. 9,511,041.

(Continued)

*Primary Examiner* — Craig D Ricci
(74) *Attorney, Agent, or Firm* — Goodwin Procter LLP

(57) ABSTRACT

The present disclosure is directed in part to methods of treating fibrosis, e.g., hepatic fibrosis and/or intestinal fibrosis, comprising administering to a patient in need thereof an effective amount of a disclosed compound.

8 Claims, 18 Drawing Sheets
Specification includes a Sequence Listing.

(56) References Cited

U.S. PATENT DOCUMENTS

| | | |
|---|---|---|
| 9,682,050 B2 | 6/2017 | Baroni et al. |
| 9,682,923 B2 | 6/2017 | Baroni et al. |
| 9,809,557 B2 | 11/2017 | Larsen et al. |
| 9,901,557 B2 | 2/2018 | Baroni et al. |
| 9,913,817 B2 | 3/2018 | Baroni et al. |
| 10,016,381 B2 | 7/2018 | Naccari et al. |
| 10,137,101 B2 | 11/2018 | Baroni et al. |
| 10,398,667 B2 | 9/2019 | Baroni et al. |
| 10,959,970 B2 | 3/2021 | Baroni et al. |
| 11,046,641 B2 | 6/2021 | Baroni et al. |
| 2003/0113815 A1 | 6/2003 | Houseknecht et al. |
| 2003/0133875 A1 | 7/2003 | Kelly |
| 2003/0220374 A1 | 11/2003 | Needleman |
| 2003/0229083 A1 | 12/2003 | Debnath et al. |
| 2004/0009956 A1 | 1/2004 | Pei et al. |
| 2004/0034067 A1 | 2/2004 | MacPhee |
| 2004/0115127 A1 | 6/2004 | Wright et al. |
| 2004/0132110 A1 | 7/2004 | Desreumaux et al. |
| 2005/0277693 A1 | 12/2005 | Palle et al. |
| 2006/0013775 A1 | 1/2006 | Gristwood et al. |
| 2006/0159648 A1 | 7/2006 | Davis et al. |
| 2006/0177444 A1 | 8/2006 | Horizoe |
| 2006/0270635 A1 | 11/2006 | Wallace et al. |
| 2007/0065471 A1 | 3/2007 | Jomard et al. |
| 2007/0086967 A1 | 4/2007 | MacDonald |
| 2007/0093524 A1 | 4/2007 | Nambi et al. |
| 2007/0149804 A1 | 6/2007 | Woltering et al. |
| 2007/0299047 A1 | 12/2007 | Maher et al. |
| 2009/0042909 A1 | 2/2009 | Karnik |
| 2009/0048343 A1* | 2/2009 | Naccari .................. A61P 35/04 514/567 |
| 2009/0054312 A1 | 2/2009 | Wolf et al. |
| 2009/0118357 A1 | 5/2009 | Naccari et al. |
| 2010/0041617 A1 | 2/2010 | Trepel et al. |
| 2010/0305077 A1 | 12/2010 | Baroni et al. |
| 2011/0105748 A1 | 5/2011 | Bhuniya et al. |
| 2011/0152225 A1 | 6/2011 | Baroni et al. |
| 2011/0288058 A1 | 11/2011 | Baroni et al. |
| 2011/0288177 A1 | 11/2011 | Baroni et al. |
| 2012/0053244 A1 | 3/2012 | Baroni et al. |
| 2012/0053245 A1 | 3/2012 | Baroni et al. |
| 2012/0100223 A1 | 4/2012 | Bhagat |
| 2012/0157417 A1 | 6/2012 | Baroni et al. |
| 2012/0195980 A1 | 8/2012 | Shaver |
| 2012/0316230 A1 | 12/2012 | Naccari et al. |
| 2013/0005813 A1 | 1/2013 | Naccari et al. |
| 2015/0045436 A1 | 2/2015 | Naccari et al. |
| 2015/0051285 A1 | 2/2015 | Baroni et al. |
| 2015/0087678 A1 | 3/2015 | Baroni et al. |
| 2015/0087708 A1 | 3/2015 | Baroni et al. |
| 2015/0148418 A1 | 5/2015 | Baroni et al. |
| 2015/0250749 A1 | 9/2015 | Giuliani et al. |
| 2015/0265514 A1 | 9/2015 | Giuliani et al. |
| 2015/0265562 A1 | 9/2015 | Naccari et al. |
| 2015/0265563 A1 | 9/2015 | Naccari et al. |
| 2016/0160867 A1 | 6/2016 | Gehlot |
| 2016/0338927 A1 | 11/2016 | Baroni et al. |
| 2017/0056349 A1 | 3/2017 | Baroni et al. |
| 2017/0172956 A1 | 6/2017 | Baroni et al. |
| 2017/0312239 A1 | 11/2017 | Naccari et al. |
| 2018/0064667 A1 | 3/2018 | Baroni et al. |
| 2018/0065921 A1 | 3/2018 | Baroni et al. |
| 2018/0099920 A1 | 4/2018 | Holm Pedersen et al. |
| 2018/0193361 A1 | 7/2018 | Winer et al. |
| 2018/0222880 A1 | 8/2018 | Wang et al. |
| 2018/0369178 A1 | 12/2018 | Baroni et al. |
| 2019/0046490 A1 | 2/2019 | McNulty et al. |
| 2019/0269637 A1 | 9/2019 | Baroni et al. |
| 2020/0188340 A1 | 6/2020 | Baroni et al. |
| 2020/0383942 A1 | 12/2020 | Baroni et al. |
| 2021/0113505 A1 | 4/2021 | Giuliani et al. |
| 2022/0000818 A1 | 1/2022 | Bellinvia et al. |
| 2022/0194894 A1 | 6/2022 | Demartis et al. |
| 2022/0354509 A1 | 11/2022 | Narducci et al. |

FOREIGN PATENT DOCUMENTS

| | | |
|---|---|---|
| CN | 105566153 A | 5/2016 |
| EP | 0055689 A1 | 7/1982 |
| EP | 0102833 A1 | 3/1984 |
| EP | 0115419 A2 | 8/1984 |
| EP | 0279096 A2 | 8/1988 |
| EP | 0291159 A2 | 11/1988 |
| EP | 0352826 A2 | 1/1990 |
| EP | 0623104 B1 | 8/1997 |
| EP | 0938459 B1 | 7/2002 |
| EP | 1285908 A1 | 2/2003 |
| EP | 1348698 A1 | 10/2003 |
| EP | 0554291 B1 | 12/2003 |
| EP | 1373906 A1 | 1/2004 |
| EP | 1389044 A1 | 2/2004 |
| EP | 1607103 A1 | 12/2005 |
| EP | 1274407 B1 | 3/2006 |
| EP | 1719543 A1 | 11/2006 |
| EP | 1801093 B1 | 3/2009 |
| EP | 1448995 B1 | 1/2011 |
| EP | 2298321 A1 | 3/2011 |
| EP | 2107047 B1 | 9/2011 |
| EP | 2926807 A1 | 10/2015 |
| GB | 767788 A | 2/1957 |
| GB | 1359560 | 7/1974 |
| JP | 2003-516310 A | 5/2003 |
| JP | 3425441 B2 | 7/2003 |
| JP | 3435651 B2 | 8/2003 |
| JP | 2004-528329 A | 9/2004 |
| JP | 2005-510733 A | 4/2005 |
| JP | 2009-242399 A | 10/2009 |
| JP | 2010-520166 A | 6/2010 |
| JP | 2015-506193 A | 3/2015 |
| JP | 2015-518483 A | 7/2015 |
| WO | WO-1992/006690 A1 | 4/1992 |
| WO | WO-1993/014056 A1 | 7/1993 |
| WO | WO-93/19053 A1 | 9/1993 |
| WO | WO-1994/000135 A1 | 1/1994 |
| WO | WO-1995/031194 A1 | 11/1995 |
| WO | WO-1996/030016 A1 | 10/1996 |
| WO | WO-1997/025042 A1 | 7/1997 |
| WO | WO-1998/006387 A2 | 2/1998 |
| WO | WO-1998/043081 A1 | 10/1998 |
| WO | WO-1999/015520 A1 | 4/1999 |
| WO | WO-1999/29317 A1 | 6/1999 |
| WO | WO-2000/059866 A1 | 10/2000 |
| WO | WO-2000/062766 A2 | 10/2000 |
| WO | WO-2001/002388 A1 | 1/2001 |
| WO | WO-2001/025181 A1 | 4/2001 |
| WO | WO-2001/066067 A1 | 9/2001 |
| WO | WO-2001/079153 A1 | 10/2001 |
| WO | WO-2002/046161 A1 | 6/2002 |
| WO | WO-2002/077651 A2 | 10/2002 |
| WO | WO-2002/085123 A1 | 10/2002 |
| WO | WO-2002/095393 A2 | 11/2002 |
| WO | WO-2003/033456 A1 | 4/2003 |
| WO | WO-2003/033481 A1 | 4/2003 |
| WO | WO-2003/043569 A2 | 5/2003 |
| WO | WO-2003/046580 A1 | 6/2003 |
| WO | WO-2003/048116 A2 | 6/2003 |
| WO | WO-2003/053974 A1 | 7/2003 |
| WO | WO-2004/037810 A1 | 5/2004 |
| WO | WO-2004/073622 A2 | 9/2004 |
| WO | WO-2005/012280 A1 | 2/2005 |
| WO | WO-2005/040102 A2 | 5/2005 |
| WO | WO-2005/072113 A2 | 8/2005 |
| WO | WO-2005/084658 A1 | 9/2005 |
| WO | WO-2006/072175 A1 | 7/2006 |
| WO | WO-2007/010514 A2 | 1/2007 |
| WO | WO-2007/010516 A2 | 1/2007 |
| WO | WO-2007/096148 A1 | 8/2007 |
| WO | WO-2008/094618 A2 | 8/2008 |
| WO | WO-2008/104557 A1 | 9/2008 |
| WO | WO-2009/025854 A2 | 2/2009 |
| WO | WO-2009/080828 A2 | 7/2009 |
| WO | WO-2009135911 A1 | 11/2009 |
| WO | WO-2010/063470 A2 | 6/2010 |
| WO | WO-2010/063472 A1 | 6/2010 |

(56) References Cited

FOREIGN PATENT DOCUMENTS

| WO | WO-2010/091894 A2 | 8/2010 |
|---|---|---|
| WO | WO-2010091892 A2 | 8/2010 |
| WO | WO-2013/012662 A2 | 1/2013 |
| WO | WO-2013/059364 A2 | 4/2013 |
| WO | WO-2013/064153 A1 | 5/2013 |
| WO | WO-2013/117744 A9 | 8/2013 |
| WO | WO-2013/156413 A1 | 10/2013 |
| WO | WO-2013/168438 A1 | 11/2013 |
| WO | WO-2013/178815 A1 | 12/2013 |
| WO | WO-2013/178816 A1 | 12/2013 |
| WO | WO-2014/041140 A1 | 3/2014 |
| WO | WO-2014/041141 A1 | 3/2014 |
| WO | WO-2014/154683 A1 | 10/2014 |
| WO | WO-2016/154730 A1 | 10/2016 |
| WO | WO-2016/202341 A1 | 12/2016 |
| WO | WO-2017/046343 A1 | 3/2017 |
| WO | WO-2017/093444 A1 | 6/2017 |
| WO | WO-2017/144725 A1 | 8/2017 |
| WO | WO-2020152350 A1 | 7/2020 |
| WO | WO-2020/161362 A1 | 8/2020 |

OTHER PUBLICATIONS

U.S. Appl. No. 15/337,707, Alkylamido Compounds and Uses Thereof, filed Oct. 28, 2016, U.S. Pat. No. 10,137,101.
U.S. Appl. No. 16/733,349, Alkylamido Compounds and Uses Thereof, filed Jan. 3, 2020, Published U.S. 2020-0383942.
U.S. Appl. No. 13/131,982, Methods of Preventing or Reducing Colon Carcinogenesis, filed Aug. 11, 2011, U.S. Pat. No. 8,501,806.
U.S. Appl. No. 12/528,522, PPAR-Gamma Agonists for the Induction of Cationic Antimicrobial Peptide Expression as Immunoprotective Stimulants, filed Mar. 4, 2011, Abandoned.
U.S. Appl. No. 13/201,790, Methods of Treating Hair Related Conditions, filed Nov. 17, 2011, U.S. Pat. No. 8,796,334.
U.S. Appl. No. 14/314,738, Methods of Treating Hair Related Conditions, filed Jun. 25, 2014, Abandoned.
U.S. Appl. No. 14/969,939, Methods of Treating Hair Related Conditions, filed Dec. 15, 2015, U.S. Pat. No. 9,901,557.
U.S. Appl. No. 15/872,436, Methods of Treating Hair Related Conditions, filed Jan. 16, 2018, U.S. Pat. No. 10,398,667.
U.S. Appl. No. 16/515,532, Methods of Treating Hair Related Conditions, filed Jul. 18, 2019, U.S. Pat. No. 10,959,970.
U.S. Appl. No. 17/181,015, Methods of Treating Hair Related Conditions, filed Feb. 22, 2021, Pending.
U.S. Appl. No. 11/989,090, Compounds and Their Salts Specific to the PPAR Receptors and the EGF Receptors and their Use in the Medical Field, filed Jun. 6, 2008, U.S. Pat. No. 8,153,841.
U.S. Appl. No. 13/408,439, Compounds and Their Salts Specific to the PPAR Receptors and the EGF Receptors and Their Use in the Medical Field, filed Feb. 29, 2012, U.S. Pat. No. 8,710,100.
U.S. Appl. No. 14/202,386 Compounds and Their Salts Specific to the PPAR Receptors and the EGF Receptors and Their Use in the Medical Field, filed Mar. 10, 2014, U.S. Pat. No. 9,133,099.
U.S. Appl. No. 14/671,579, Compounds and Their Salts Specific to the PPAR Receptors and the EGF Receptors and Their Use in the Medical Field, filed Mar. 27, 2015, U.S. Pat. No. 9,561,202.
U.S. Appl. No. 14/671,585, Compounds and Their Salts Specific to the PPAR Receptors and the EGF Receptors and Their Use in the Medical Field, filed Mar. 27, 2015, U.S. Pat. No. 9,345,680.
U.S. Appl. No. 15/377,013, Compounds and Their Salts Specific to the PPAR Receptors and the EGF Receptors and Their Use in the Medical Field, filed Dec. 13, 2016, U.S. Pat. No. 10,016,381.
U.S. Appl. No. 11/989,033, Compounds and Their Salts Specific to the PPAR Receptors and EGF Receptors and Their Use in the Medical Field, filed Jun. 6, 2008, U.S. Pat. No. 8,138,357.
U.S. Appl. No. 13/397,245, Compounds and Their Salts Specific to the PPAR Receptors and EGF Receptors and Their Use in the Medical Field, filed Feb. 15, 2012, U.S. Pat. No. 8,450,506.
U.S. Appl. No. 13/785,485, Compounds and Their Salts Specific to the PPAR Receptors and EGF Receptors and Their Use in the Medical Field, filed Mar. 5, 2013, Abandoned.
U.S. Appl. No. 12/810,159, Compounds for the Selective Treatment of the Intestinal Immuno-Inflammatory Component of the Celiac Disease, filed Aug. 16, 2010, U.S. Pat. No. 8,153,693.
U.S. Appl. No. 13/331,173, Compounds for the Selective Treatment of the Intestinal Immuno-Inflammatory Component of the Celiac Disease, filed Dec. 20, 2011, Abandoned.
U.S. Appl. No. 14/377,362, Methods of Treating Fibrosis, filed Aug. 7, 2014, U.S. Pat. No. 9,682,923.
U.S. Appl. No. 15/593,864, Methods of Treating Fibrosis, filed May 12, 2017, U.S. Pat. No. 11,046,641.
U.S. Appl. No. 14/394,916, Methods of Treating Lactose Intolerance, filed Oct. 16, 2014, U.S. Pat. No. 9,682,050.
U.S. Appl. No. 15/594,023, Methods of Treating Lactose Intolerance, filed May 12, 2017, Abandoned.
U.S. Appl. No. 14/428,048, Methods of Inhibiting Hair Growth, filed Mar. 13, 2015, Abandoned.
U.S. Appl. No. 14/428,164, Methods of Treating Hair Related Conditions, filed Mar. 13, 2015, Abandoned.
Ahnfelt-Ronne et al. (1990) "Clinical Evidence Supporting the Radical Scavenger Mechanism of 5-Aminosalicylic Acid," Gastroenterology, 98(5 Pt 1):1162-9.
Allgayer (2003) "Review Article: Mechanisms of Action of Mesalazine in Preventing Colorectal Carcinoma in Inflammatory Bowel Disease," Aliment Pharmacol Ther, 18(Suppl. 2):10-4.
Ameho et al., (1997) 'Prophylactic Effect of Dietary Glutamine Supplementation on Interleukin 8 and Tumor Necrosis Factor Alpha Production in Trinitrobenzene Sulphonic Acid Induced Colitis,' Gut, 41(4):487-93.
Australian Examination Report dated Jan. 31, 2014, for Application No. 2009321722 (9 pages).
Azhar, (2010), 'Peroxisome Proliferator-Activated Receptors, Metabolic Syndrome and Cardiovascular Disease,' Future Cardiol, 6(5):657-91 (NIH Public Access Author Manuscript).
Baker et al., (1962) "Potential Anticancer Agents. LXXVIII Nonclassical Antimetabolites. IV. Synthesis of Compounds Related to 4-(Iodoacetamido) Salicylie Acid, an Exo-Alkylating Irreversible Inhibitor," J Org Chem, 27(9):3283-95.
Bassaganya-Riera, et al "Activation of PPAR γ and δ by conjugated linoleic acid mediates protection from experimental inflammatory bowel disease," Gastroenterology, 127(3): 777-791, (2004).
Baz et al. (2003) 'Oxidant / Antioxidant Status in Patients with Psoriasis,' Yonsei Med J, 44(6):987-90.
Behshad et al., (2008) 'A Retrospective Case Series Review of the Peroxisome Proliferator-Activated Receptor Ligand Rosiglitazone in the Treatment of Atopic Dermatitis,' Arch Dermatol, 144(1):84-8.
Beilstein Database Beistein Institute zur Forderung der Chemischen Wissenschaften, Frankfurt an Main, DE XP002413839, Accession No. 2092096, J. Med. Chem., 22: 589 (1979).
Beilstein Database, Beilstein Institute for Organic Chemistry, Frankfurt an Main, DE, retrieved from XFIRE, Accession No. brn 2208094, J. Am. Chem. Soc., 68: 2335, 2338 (1946).
Beilstein Database, Beilstein Institute for Organic Chemistry, Frankfurt an Main, DE, retrieved from XFIRE, Accession No. brn 2803076, J. Org. Chem., 14: 1013, 1018 (1949).
Beilstein Database, Beilstein Institute for Organic Chemistry, Frankfurt an Main, DE, retrieved from XFIRE, Accession No. brn 3199913, Chem. Ber., 46: 3978 (1913).
Beilstein Database, Beilstein Institute for Organic Chemistry, Frankfurt an Main, DE, retrieved from XFIRE, Accession No. brn 3200601, J. Chem. Soc., pp. 104, 111 (1935).
Beilstein Database, Beilstein Institute for Organic Chemistry, Frankfurt an Main, DE, retrieved from XFIRE, Accession No. brn 3268495, Justus Liebigs Ann. Chem., 463:60 (1924).
Beilstein Database, Beilstein Institute for Organic Chemistry, Frankfurt an Main, DE, retrieved from XFIRE, Accession No. brn 3296969, Chem. News J. Ind. Sci, 36: 269 (1877).
Beilstein Database, Beilstein Institute for Organic Chemistry, Frankfurt an Main, DE, retrieved from XFIRE, Accession No. pcrn 859019, U.S. Pat. No. 4,429,152 A (Jan. 1984).

(56) References Cited

OTHER PUBLICATIONS

Beilstein Database, Beilstein Institute for Organic Chemistsry, Frankfurt an Main, DE, retrieved from XFIRE, Accession No. brn 3199917, Chem. Ber., 46: 288 (1913).
Beilstein Database, Beilstsein Institute for Organic Chemistry, Frankfurt an Main, DE, retrieved from XFIRE, Accession No. brn 3242057, Chem. Ber., 74: 500, 517 (1941).
Beilstein Database, Beistein Institut zur Forderung der Chemischen Wissenschaften, Frankfurt an Main, DE, XP002413837, Accession No. 2367395, Chem. Ber., 87: 179-181 (1954.).
Beilstein Database, Beistein Institut zur Forderung der Chemischen Wissenschaften, Frankfurt an Main, DE, XP002413838, Accession No. 2839685, J. Am. Chem Soc., 73: 903-904 (1951).
Beilstein Database, Beistein Institut zur Forderung der Chemischen Wissenschaften, Frankfurt an Main, DE, XP002413840, Accession No. 3031462, Bull Soc. Chim Belg., 61: 310-320 (1952).
Beilstein Database, Beistein Institut zur Forderung der Chemischen Wissenschaften, Frankfurt an Main, DE, XP002413842, Accession No. 3259704, Justus Liebigs Ann Chem, 429: 173 (1922).
Beilstein Database, Beistein Institut zur Förderrung der Chemischen Wisssenschaften, Frankfurt an Main, DE, XP002413836, Accession No. 1869425, J. Labelled Compd Radiopharm, 44: S225-S227 (2001).
Beilstein Database, Beisten Insstitut zur Forderung der Chemischen Wissenschaften, Frankfurt an Main, DE, XP002413843, Accession No. 3530419, Justus Liebigs Ann Chem, 429: 164 (1922).
Beilstein Database, Beisten Institut zur Forderung der Chemischen Wissenschaften, Frankfurt an Main, DE, XP002413841, Accession No. 2641495, J. Org. Chem., 27: 3283-3295 (1962).
Bickers et al., (2006) 'Oxidative Stress in the Pathogenesis of Skin Disease,' J Invest Dermatol, 126(2):2565-75.
Bongartz et al., (2005) 'Treatment of Active Psoriatic Arthritis with the PPARy Ligand Pioglitazone: An Open-Label Pilot Study,' Rheumatology, 44(1):126-9.
Broadwith (2009) "Enzyme Binds Both Sides of the Mirror," Chem World, Nov. 6, 2009, https://www.chemistryworld.com/news/enzyme-binds-both-sides-of-the-mirror/1016647.article (2 pages).
Brown and Joyeau, (1979), 'Use of p-Aminophenyl D and L-Lactic Acids and p-Aminophenyl Pyruvic Acid as Effectors in the Affinity Chromatography of Lactate Dehydrogenase,' Biochimie, 61(3):437-42 (Abstract only).
Brown et al., (1978) "Chimie Organique," C.R. Acad. Sc. Paris, t. 287:125-8.
Brunton et al., (1997) "A Role of Epidermal Growth Factor Receptor, c-Src and Focal Adhesion Kinase in an in vitro Model for the Progression of Colon Cancer," Oncogene, 14( 3):283-93.
Bull (2003) "The Role of Peroxisome Proliferator-Activated Receptor y in Colon Cancer and Inflammatory Bowel Disease," Arch Pathol Lab Med, 127(9):1121-3.
CAPLUS file accession No. 2007:857379, document No. 148:517389, Indian patent No. IN2003CH01004, published on Jul. 27, 2007.
Casen Recordati Group, (2016), 'Cleen Ready-to-Use Enema, Summary of Product Characteristics Updated Jun. 16, 2016,' emc+, medicines.org.UK/emc, XP-002763390, <https://www.medicines.org.UK/emc/print-document?documentld-542>, [retrieved Oct. 25, 2016] (5 pages).
Casen Recordati Group, (2016), 'Cleen Ready-to-Use Enema,' emc+, medicines.org.UK/emc, XP-002763391, <https://www.medicines.org.UK/emc/history/542#version9>, [retrieved Oct. 25, 2016] (2 pages).
Clark et al., (1989) "Validation of the General Purpose Tripos 5.2 Field," J. Comput Chem, 10(8):982-1012.
Collino et al., (2006) "Modulation of the Oxidative Stress and Inflammatory Response by PPAR-gamma Agonists in the Hippocampus of Rats Exposed to Cerebral Ischemia/Reperfusion," Eur J Pharmacol, 530(1-2):70-80.
Corse et al., (1948) "Biosynthesis of Penicillins" J Am Chem Soc, 70(9):2837-43.
Database CA [Online] Chemical Abstracts Service, Columbus Ohio, US; Database Accession No. 67:50608, Abstract of Baker et al.: "Irreversible Enzyme Inhibitors. LXXXVII. Hydrophobic Bonding to dihydrofolic reductase. 9. Mode of Binding of m-aryloxyalkyl groups on, 6-diamino-1,2-dihydro-2,2-dimethyl-1-phenyl-s-triazine", (1967).
Database CA [Online] Chemical Abstracts Service, Columbus, Ohio, US, Database Accession No. 107:235800, Abstract of Cleary, et al., "Methylenecyclopropane rearrangement as a probe for free radical substituent effects . . . sigma . . . bul. Values for commonly encountered conjugating and organometallic groups", (1987).
Database CA [Online] Chemical Abstracts Service, Columbus, Ohio, US, Database Accession No. 111:153586, Abstract of Gonzalez, et al., ".alpha.-Amino carbanions. A second generation formamidine for facile deprotonation leading to .alpha.-quaternary substitution", (1989).
Database CA [Online] Chemical Abstracts Service, Columbus, Ohio, US, Database Accession No. 119:95018, Abstract of Yoon, et al., "Reduction of nitro compounds with borohydride exchange resin—nickel acetate", (1993).
Database CA [Online] Chemical Abstracts Service, Columbus, Ohio, US, Database Accession No. 131:144358, Abstract of Lamy-Pitara, et al., "Selective Catalytic Hydrogenation of Unsaturated Derivatives of Nitrobenzene in Alcoholic Media", (1999).
Database CA [Online] Chemical Abstracts Service, Columbus, Ohio, US, Database Accession No. 50:52519, Abstract of Pratt, et al., "Reaction rates by distillation. VI. The etherification of benzyl and related alcohols", (1956).
Database CA [Online] Chemical Abstracts Service, Columbus, Ohio, US, Database Accession No. 8:526, Abstract of Schepss, "Electrolytic reduction of aldehydes", (1914).
Database CA [Online] Chemical Abstracts Service, Columbus, Ohio, US, Database Accession No. 2010:351508, Abstract of Baroni, et al., "Compounds for the selective treatment of intestinal immuninflammatory component of the celiac disease", (2007).
Database CA [Online] Chemical Abstracts Service, Columbus, Ohio, US, Database Document No. 118:101608, Accession No. 1993:101608, Abstract of Breuer, et al., "An efficient synthesis of ethyl 3'-aminocinnamate", (1992).
Database CA [Online] Chemical Abstracts Service, Columbus, Ohio, US: Database Accession No. 96:19761, Abstract of Macek et al., "Studies on Local Anesthetics LXXIV. Basic esters of o-(m-) (alkoxymethyl)carbanilic acids", (1981).
Database CA [Online] Chemical Abstracts Service, Columbus, Ohio, US; Database Accession No. 105:24135, Abstract of Wulff, et al., "Chemistry of binding sites. VI. On the suitability of various aldehydes and ketones as binding sites for monoalcohols", (1986).
Database CA [Online] Chemical Abstracts Service, Columbus, Ohio, US; Database Accession No. 110:194186, Abstract of Pei et al., "A Lewis acid catalyst supported by polymers-styrene-methyl methacrylate copolymer-titanium tetrachloride complex preparation and uses in organic synthesis", (1989).
Database CA [Online] Chemical Abstracts Service, Columbus, Ohio, US; Database Accession No. 112:157479, Abstract of Joshi et al., "Catalysis by heteropoly acids: some new aspects", (1989).
Database CA [Online] Chemical Abstracts Service, Columbus, Ohio, US; Database Accession No. 121:204747, Abstract of Yang et al., "Photosolvolysis of 2-aminobenzyl alcohol in aqueous solution", (1994).
Database CA [Online] Chemical Abstracts Service, Columbus, Ohio, US; Database Accession No. 131:228419, Abstract of Engell et al., "The Decomposition of methyl hemiacetals of benzaldehyde in aqueous solution: a study of the effect of aromatic substitution", (1999).
Database CA [Online] Chemical Abstracts Service, Columbus, Ohio, US; Database Accession No. 135:180359, Abstract of Pitts et al., "Indium metal as a reducing agent in organic synthesis", (2001).
Database CA [Online] Chemical Abstracts Service, Columbus, Ohio, US; Database Accession No. 49:68907, Abstract of Mann, et al., "The action of magnesium and of Grignard reagents on certain benzyl ethers. II. The action of Grignard reagents on .omicron.-, m-, and p-(methoxy- and phenoxymethyl) anilines", (1954).
Database CA [Online] Chemical Abstracts Service, Columbus, Ohio, US; Database Accession No. 66:37529, Abstract of Minisci,

(56) References Cited

OTHER PUBLICATIONS et al., "Orientation in the radical amination of aromatic compounds with N-chlorodimethylamine-competition between nuclear and benzylic attack", (1966).

Database CA [Online] Chemical Abstracts Service, Columbus, Ohio, US; Database Accession No. 84:4573, Abstract of Gale, et al., "Amidomethylation of some N,N-dialkylanilines (Tscherniac-Einhorn reaction)", (1975).

Database CA Registry [Online] Chemical Abstracts Service, Columbus, Ohio, US; Database Accession No. 1001756-73-5, Abstract & "Allichem Catalog" Jun. 3, 2009; XP002595814, (2008).

Database Caplus Chemical Abstracts Service, Columbus, Ohio, US; Database Accession No. 1913:10241, Abstract of Heller: Berichte der Deutschen Chemischen Gesellschaft (1913), 46:280-294.

Database Caplus Chemical Abstracts Service, Columbus, Ohio, US; Database Accession No. 1949:23214, Abstract of Tomcsik et al.: Helvetica Chimica Acta (1949), 32:31-34.

Database Caplus Chemical Abstracts Service, Columbus, Ohio, US; Database Accession No. 1955:19868, Abstract of Mann et al.: Chemistry & Industry (London, United Kingdom) (1954) 373-374.

Database Caplus Chemical Abstracts Service, Columbus, Ohio, US; Database Accession No. 1979:18291, Abstract of Brown et al.: "Affinity Chromatography of L-lactate dehydrogenase (LDH) on Synthetic Supports. Preparation and Immobilization of D- and L-p-aminophenyllactic Acids, New Effectors of LDH." Comptes Rendus des Seances de l'Academic des Scie. 287(4):125-128 (1978).

Database Caplus Chemical Abstracts Service, Columbus, Ohio; Database Accession No. 1925:25469, Abstract of Sherwin: "Acetylation as a Physiologic Reaction." Proceedings of the Society for Experimental Biology and Medicine (1924), 22:182.

Database Caplus Chemical Abstracts Service, Columbus, Ohio; Database Accession No. 1967:490291, Abstract of Deljac et al.: "Absolute Configuration of (--) -β-hydroxy-β-(m-hydroxyphenyl) propionic acid", Recueill des Travaux Chimiques des Pays-Bas (1967), 68(8):765-768.

Database Chemcats [Online] Chemical Abstracts Service, Columbus, Ohio, US; Accession No. 2058162244, Allichem Product List, Jun. 3, 2009; XP002591674, Feb. 6, 2008.

Delbarre et al., (1964), "Chemical Abstracts, vol. 65, Columbus , Ohio, Abstract No. 93711, "Nonsteroid Antiinflammatory Substances. I. Derivatives of the 4- and 5- Aminosalicylic Acids, Med Exp Int J Exp Med, 11:389-96.

Deljac et al., (1967) "Absolute Configuration of (-)-β-Hydroxy-β-(m)-Hydroxyphenyl)-Propionic Acid," Recueil des Travaux Chimiques des Pays-Bas, 86:765-8.

Di Gregorio, J. et al. "Role of glycogen synthase kinase-3? and PPAR-? on epithelial-to-mesenchymal transition in DSS-induced colorectal fibrosis," PLoS One (2017), 12(2), e0171093/1-e0171093/23.

Dimon-Gadal et al., (2000) 'Increased Oxidative Damage to Fibroblasts in Skin With and Without Lesions in Psoriasis,' J Invest Dermatol, 114(5):984-9.

Ding, et al., (2012) "Mucosal Healing and Fibrosis after Acute or Chronic Inflammation in Wild Type FVB-N Mice and C57BL6 Procollagen α1(I)-Promoter-GFP Reporter Mice",PLoS One, vol. 7, No. 8, p. e42568, XP055433727.

Dipoï et al., (2004) 'Functions of Peroxisome Proliferator-Activated Receptors (PPAR) in Skin Homeostasis,' Lipids, 39(11):1093-9.

DiPoï et al., (2005) 'Epithelium-Mesenchyme Interactions Control the Activity of Peroxisome Proliferator-Activated Receptor β/δ During Hair Follicle Development,' Mol Cell Biol, 25(5):1696-1712(2005).

Doshi et al., (1997) "A Comparison of Current Acne Grading Systems and Proposal of a Novel System," Int J Dermatol, 36(6):416-8.

Drosner M et al., (2005), 'Photo-Epilation: Guidelines for Care from the European Society for Laser Dermatology (ESLD),' J Cosmet Laser Ther, 7(1):33-8.

Dubuquoy et al., (2002) "Role of peroxisome proliferator-activated receptor γ and retinoid X receptor heterodimer in hepatogastroenterological diseases," Lancet, 360(9343):1410-8.

Dubuquoy et al., (2003) "Impaired Expression of Peroxisome Proliferator-Activated Receptor Gamma in Ulcerative Colitis," Gastroenterology, 124(5):1265-76.

Dyall-Smith, D, "Lichen Planopilaris,", 2011, pp. 1-4 [online] [retrieved on Mar. 29, 2018] Retrieved from http://www.dermnetnz.org/topics/lichen-planopilaris.

Egan et al., (2003) "Clinical Pharmacology in Inflammatory Bowel Disease: Optimizing Current Medical Therapy," *Inflammatory Bowel Disease: From Bench to Bedside*, (2*nd* Ed, 2003), Stephan R Targan et al. (Eds), Springer Publishingm New York, NY (Publ), pp. 495-521.

Ellis et al., (2007) "Placebo Response in Two Long-Term Randomized Psoriasis Studies that were Negative for Rosiglitazone," Am J Clin Dematol, 8(2):93-102.

European Clinical Trials Register, (2012), entry EudraCT No. 2011-003283-78 [online] Mar. 1, 2012, [retrieved from the internet at <https://www.clinicaltrialsregister.eu/ctr-search/trial/2011-003283-78/IT> on Feb. 1, 2017] European Union Clinical Trials Register, XO-002766683 (6 pages).

Examination Report dated Apr. 15, 2011 for Application No. 06 766 083.7-2103 (11 pages).

Fernholz et al., (1992) "Specificity of Antibody-Catalyzed Transesterifications Using Enol Esters: A Comparison with Lipase Reactions," J Org Chem, 57(17):4756-61.

Floch and White, (2006), 'Management of Diverticular Disease is Changing,' World J Gastroenterol, 12(20):3225-8.

Fuenzalida et al., (2007) "Peroxisome Proliferator-activated Receptor Gamma Up-regulates the Bcl-2 Anti-apoptotic Protein in Neurons and Induces Mitochondrial Stabilization and Proection against Oxidative Stress and Apoptosis," J Biol Chem, 282(51):37006-15.

Gampe et al., (2000) "Asymmetry in the PPARγ/RXRα Crystal Structure Reveals the Molecular Basis of Heterodimerization Among Nuclear Receptors," Mol Cell, 5(3):545-55.

Garza LA et al., (2011), 'Bald Scalp in Men with Androgenetic Alopecia Retains Hair Follicle Stem Cells but Lacks CD200-Rich and CD34-Positive Hair Follicle Progenitor Cells,' J Clin Invest, 121(2):613-22.

Gerdes et al., (1986) "Growth Fractions in Breast Cancers Determined in Situ with Monoclonal Antibody Ki-67," J Clin Pathol, 39(9):977-80.

GlaxoSmithKline. (2008) Scientific Result Summary for Clinical Study ID 49653/292. "A Randomized, Double-Blind, Placebo-Controlled Trial to Assess Three Dose Levels of Rosiglitazone Maleate in the Treatment of Moderate to Severe Plaque Psoriasis," [retrieved from <https://www.gsk-clinicalstudyregister.com/study/49653/292> on Jul. 25, 2017] (3 pages).

Gormin (1989), "Picosecond Transient Absorption Spectra of Aminosalicylates in Confirmation of the Triple Excitation Mechanism," J Phys Chem, 93(16):5979-80.

Guo et al., (2009) "Effect of Uyghur Compound Xipayi Kui Jie'an on the Ultrastructure of Small Intestinal Epithelial Cell in Rat Model of Ulcerative Colitis," J Xinjiang Medi Univ, 32(7):893-4.

Haemmerli U P et al. (1965) "Acquired milk intolerance in the adult caused by lactose malabsorption due to a selective deficiency of intestinal lactase activity," American Journal of Medicine, vol. 38, pp. 7-30.

Harari (2004) "Epidermal Growth Factor Receptor Inhibition Strategies in Oncology," Endocr Relat Cancer, 11(4):689-708.

Harrington et al., (2008) 'A Re-appraisal of Lactose Intolerance,' Int J Clin Pract, 62(10):1541-6.

Harrison et al., "Cows' milk protein intolerance: a possible association with gastroenteritis, lacctose intolerance, and IgA deficiency," British Medical Journal 1:1501-1504 (1976).

Highlights of Prescribing Information Actos (pioglitazone hydrochloride), Revised Jul. 2011, Retrieved from the Internet (URL): <https://www.accessdata.fda.gov/drugsatfda_docs/label/2011/021073s043s044lbl.pdf>, 43 pages.

Honeder et al. "Improvement of replication fidelity by certain mesalazine derivatives", International Journal of Oncology (2012), 40(5), 1331-1338.

(56) References Cited

OTHER PUBLICATIONS

Husova et al., (2007) "Hepatopathy, Coeliac Disease and Lymphocytic Colitis," Ceska A. Slovenska Gastroenterologie A. Hepatologie—CZ SL Gastroenterol Hepatol, 61(6):309-13.
Hyams et al., "Cancer Chemotherapy-Induced Lactose Malabsorption in Children," Cancer 49:646-650(1982).
International Preliminary Report on Patentability and Written Opinion of the International Searching Authority for PCT/IE2006/000076, dated Jan. 22, 2008 (10 pages).
International Preliminary Report on Patentability and Written Opinion of the International Searching Authority for PCT/EP13/057729, dated Oct. 21, 2014 (6 pages).
International Preliminary Report on Patentability and Written Opinion of the International Searching Authority for PCT/EP2009/008631, dated Jun. 7, 2011(13 pages).
International Preliminary Report on Patentability and Written Opinion of the International Searching Authority for PCT/EP2009/008633, dated Jun. 7, 2011 (6 pages).
International Preliminary Report on Patentability and Written Opinion of the International Searching Authority for PCT/EP2010/000935, dated Aug. 16, 2011 (7 pages).
International Preliminary Report on Patentability and Written Opinion of the International Searching Authority for PCT/EP2010/000939, dated Aug. 16, 2011 (8 pages).
International Preliminary Report on Patentability and Written Opinion of the International Searching Authority for PCT/EP2013/052617, dated Aug. 12, 2014 (5 pages).
International Preliminary Report on Patentability and Written Opinion of the International Searching Authority for PCT/EP2013/069062, dated Mar. 17, 2015 (7 pages).
International Preliminary Report on Patentability and Written Opinion of the International Searching Authority for PCT/EP2013/069063, dated Mar. 17, 2015 (7 pages).
International Preliminary Report on Patentability and Written Opinion of the International Searching Authority for PCT/IE2006/000078, dated Jan. 22, 2008 (14 pages).
International Preliminary Report on Patentability for PCT/EP2008/052354, completed May 22, 2009 (20 pages).
International Preliminary Report on Patentability for PCT/EP2008/068265, completed Apr. 12, 2010 (11 pages).
International Search Report and Written Opinion of the International Search Authority for International Application No. PCT/EP2016/071995—dated Jan. 16, 2017 (21 pages total).
International Search Report and Written Opinion of the International Search Authority for International Application No. PCT/EP2017/054526—dated Feb. 6, 2017 (20 pages total).
International Search Report and Written Opinion of the International Searching Authority for International Application No. PCT/EP2016/079512 dated Feb. 28, 2017 (15 pages).
International Search Report and Written Opinion of the International Searching Authority for PCT/IE2006/000078, dated Jan. 26, 2007 (14 pages).
International Search Report for PCT/EP2008/052354, dated Jun. 9, 2008 (6 pages).
International Search Report for PCT/EP2008/068265, dated Aug. 11, 2009 (5 pages).
International Search Report for PCT/EP2009/008631, dated Aug. 19, 2010 (9 pages).
International Search Report for PCT/EP2009/008633, dated Feb. 22, 2010 (4 pages).
International Search Report for PCT/EP2010/000935 dated Aug. 23, 2010 (5 pages).
International Search Report for PCT/EP2010/000939 dated Sep. 20, 2010 (5 pages).
International Search Report for PCT/EP2013/052617, dated Aug. 12, 2014 (4 pages).
International Search Report for PCT/EP2013/057729, dated Jun. 11, 2013 (4 pages).
International Search Report for PCT/EP2013/069062, dated Dec. 10, 2013 (3 pages).
International Search Report for PCT/EP2013/069063, dated Dec. 20, 2013 (3 pages).
International Search Report for PCT/IE2006/000076, dated Feb. 1, 2007 (5 pages).
Ireland et al., (1992) "Comparison of 5-Aminosalicylic Acid and N-Acetylaminosalicylic Acid Uptake by the Isolated Human Colonic Epithelial Cell," Gut, 33(10):1343-7.
Janda et al., (1988) "Antibody Catalysis of Bimolecular Amide Formation," J Am Chem Soc, 110(14):4835-7.
Jiang J et al. (1997) "Conjugated Linoleic Acid in Swedish dairy products with special reference to the manufacture of hard cheeses," International Dairy Journal, vol. 7, No. 12, pp. 863-867.
Johnson et al., (2012) 'Intestinal Fibrosis is Reduced by Early Elimination of Inflammation in a Mouse Model of IBD: Impact of a "Top-Down" Approach to Intestinal Fibrosis in Mice,' Inflamm Bowel Dis, 18(3):460-71.
Jones et al., (1997) "Development and Validation of a Genetic Algorithm for Flexible Docking," J Mol Biol, 267(3):727-48.
Julien et al., (2005) 'Antifibrogenic Role of the Cannabinoid Receptor CB2 in the Liver,' Gastroenterology, 128(3):742-55.
Kari et al., (2003) "Targeting the Epidermal Growth Factor Receptor in Cancer: Apoptosis Takes Center Stage," Cancer Res, 63(1):1-5.
Karnik et al., (2009) 'Hair Follicle Stem Cell-specific PPARγ Deletion Causes Scarring Alopecia,' J Invest Dermatol, 129(5):1243-57.
Kermani et al., Mayo Clin Proc. 2003, 78, 1088-1091.
Kloepper et al., (2008) 'Immunophenotyping of the Human Bulge Region: The Quest to Define Useful in situ Markers for Human Epithelial Hair Follicle Stem Cells and their Niche,' Exp Dermatol, 17(7):592-609.
Koeffler, (2003), "Peroxisome Proliferator-activated Receptor γ and Cancers," Clin Cancer Res, 9(1):1-9.
Kuenzli and Saurat, (2003) 'Effect of Topical PPARβ/δ and PPARγ Agonists on Plaque Psoriasis: A Pilot Study,' Dermatology, 206(3):252-6.
Lakshminarayana, N. et al. "Synthesis and evaluation of some novel isochromancarboxylic acid derivatives as potential anti-diabetic agents", European Journal of Medicinal Chemistry (2009), 44(8),3147-3157.
Lavker RM et al., (2003), 'Hair Follicle Stem Cells,' J Investig Dermatol Symp Proc, 8(1):28-38.
Lees et al., (2008) 'Analysis of Germline GLI1 Variation Implicates Hedgehog Signalling in the Regulation of Intestinal Inflammatory Pathways,' PLoS Med, 5(12):e239 (15 pages).
Levi et al., "Synthesis of O-acetyl-?-[N-[p-bis(2-chloroethyl)]-aminophenyl]latic acid ethyl ester," Zhurnal Organicheskoi Khimii (1967), 3(5), 857-61 (Abstract only).
Li et al. "Molecular recognition of nitrated fatty acids by PPARγ/" Nat. Struct. Mol. Biol. 2008, 15(8), 865-867.
Li L and Xie T, (2005), 'Stem Cell Niche: Structure and Function,' Annu Rev Cell Dev Biol, 21:605-31.
Liao et al., (1990) 'Therapeutic Effect of Methyl 5-Aminosalicylate on Experimental Ulcerative Colitis in Rabbits,' Acta Pharmacologica Sinica 11(1):54-6.
Lin et al., (1998) "An Antibody Transesterase Derived from Reactive Immunization that Utilizes a Wide Variety of Alcohol Substrates," Chem Commun, 10:1075-6.
Lowe, D. (2009) "More Binding Site Weirdness," CORANTE: In the Pipeline, pp. 1-4.
Lukovac S et al (2008) "Essential Fatty Acid (EFA) Deficiency in Mice Impairs Lactose Digestion", Abstract M1730, Annual Meeting of the American Gastroenterological Association (AGA) Institute and Digestive Disease Week, May 17-22, 2008, San Diego, CA, Gastroenterology, vol. 134, No. 4, Supplement 1, pp. A-406-A407.
Luna et al. "Oral agents in the management of type 2 diabetes mellitus." Am Fam Physician 63, 1747-1756, 2001 (10 pages).
Mager et al., (1979) "Struktur-Wirkungs-Beziehungen bei Salizylsaure-und Benzoesaurederivaten," Zbl. Pharm. 118(Heft 12):1259-75 (concise explanation of relevance attached).
Mandt N et al., (2005), 'Epilation Today: Physiology of the Hair Follicle and Clinical Photo-Epilation,' J Investig Dermatol Symp Proc, 10(3):271-4.

(56) References Cited

OTHER PUBLICATIONS

Mangelsdorf et al., (1995) "The Nuclear Receptor Superfamily: The Second Decade," Cell, 83(6):835-9.
Mastrofrancesco, M. et al. "Preclinical Studies of a Specific PPAR? Modulator in the Control of Skin Inflammation," Journal of Investigative Dermatology (2014), 134(4), 1001-1011.
Medline Database, (2013), U.S. National Library of Medicine, Bethesda, MD, XP002763389, Accession No. NLM23651165, Benjamin B et al., 'PPAR-gamma in Ulcerative Colitis: A Novel Target for Intervention,' Curr Drug Targ, 14(12):1501-7.
Medow et al., (1990) 'β-Galactosidase Tablets in the Treatment of Lactose Intolerance in Pediatrics,' Am J Dis Child, 144(11):1261-4 (Abstract).
Meek et al., (1969) "Carboxylation of Substituted Phenols in N,N-Dimethylamide Solvents at Atmospheric Pressure," J Chem Eng Data, 14(3):388-91.
Melgar, et al (2005) "Acute colitis induced by dextran sulfate sodium progresses to chronicity in C57BL6 but not in BALB/c mice: correlation between symptoms and inflammation", American Journal of Physiology—Gastrointestinal and Liver Physiology, vol. 288, No. 6, pp. G1328-G1338, XP055433729.
Mendelsohn (2001) "The Epidermal Growth Factor Receptor as a Target for Cancer Therapy," Endocr Relat Cancer, 8(1):3-9.
Merck Manual Home Edition, "Ulcerative Colitis", Merck Sharp & Dohme Corp., Copyright © 2004-2011, pp. 1-6 [online] [retrieved on Apr. 19, 2013] Retrieved from http://www.merckmanuals.com/home/print/digestive_disorders/inflammatory_bowel_diseases_ibd/ulcerative colitis.html.
Michalik and Wahli, (2007) 'Peroxisome Proliferator-activated Receptors (PPARs) in Skin Health, Repair and Disease,' Biochim Biophys Acta, 1771(8):991-8.
Mirmirani and Karnik, (2009), 'Lichen Planopilaris Treated with a Peroxisome Proliferator-Activated Receptor γ Agonist,' Arch Dermatol, 145(12):1363-6 [NIH Public Access Author Manuscript].
Misra et al., (2002) "Phosphorylation of Transcriptional Coactivator Peroxisome Proliferator-Activated Receptor (PPAR)-Binding Protein (PBP). Stimulation of Transcriptional Regulation by Mitogen-Activated Protein Kinase," J Biol Chem, 277(50): 48745-54.
Nesto, R.W et al., AHA/ADA Consensus Statement dated Dec. 9, 2003, pp. 2941-2948.
Nolte et al., (1998) "Ligand Binding and Co-Activator Assembly of the Peroxisome Proliferator-Activated Receptor-γ," Nature, 395(6698):137-43.
O'Mahony, et al., (1990) "Coeliac Disease and Collagenous Colitis," Postgrad Med, 66(773):238-41.
Office Action issued in Japanese Patent Application No. 2011-549494 dated Feb. 25, 2014, with English language translation (8 pages).
Osawa et al., (2003) "Peroxisome Proliferator-Activated Receptor γ Ligands Suppress Colon Carcinogenesis Induced by Azoxymethane in Mice," Gastroenterology, 124(2):361-7.
Oshima H et al., (2001), 'Morphogenesis and Renewal of Hair Follicles from Adult Multipotent Stem Cells,' Cell, 104(2):233-45.
Pedersen et al., (2010) 'Topical Rosiglitazone Treatment Improves Ulcerative Colitis by Restoring Peroxisome Proliferator-Activated Receptor-γ Activity,' Am J Gastroenterol, 105(7):1596-1603 (Abstract).
Pershadsingh et al., (2005) 'Improvement in Psoriasis with Rosiglitazone in a Diabetic and a Nondiabetic Patient,' Skinmed, 4(6):386-90 (Abstract).
Peyrin-Biroulet et al., (2010), 'Peroxisome Proliferator-Activated Receptor Gamma Activation is Required for Maintenance of Innate Antimicrobial Immunity in the Colon,' Proc Natl Acad Sci USA, 107(19):8772-7.
Peyrin-Biroulet, et al. (2007) "Peroxisome Proliferator-Activated Receptor Gamma Functions as an Antibacterial Factor," J Crohns Colitis Suppl, 1(1):2.
Ponchant et al., (1991) Synthesis of 5-[$^{125}$I]-Iodo-Zacopride, a New Probe for 5-HT$_3$ Receptor Binding Sites, Journal of Labelled Compounds and Radiopharmaceuticals, 29(10):1147-55.

Porter and Ihrig, (1923), 'Asymmetric Dyes,' J Am Chem Soc, 45(8):1990-3 (Abstract only).
Ramprasad et al., (2002) 'Sustained-Delivery of Apolipoprotein E-peptidomimetic Using Multivesicular Liposomes Lowers Serum Cholesterol Levels,' J Control Release, 79(1-3):207-18.
Rathi, (2011), 'Acne Vulgaris Treatment: The Current Scenario,' Indian J Dermatol, 56(1):7-13.
Reifen, Ram, et al. (2004) "5-ASA and Lycopene Decrease the Oxidative Stress and Inflammation Induced by Iron in Rats with Colitis," J Gastroenterol, 3996):514-9.
Result Summary for Study ID No. SB-999910/150 (2002) "A Study in Patients with Crohn's Disease to Evaluate the Effect of Avandia™ on Inflammatory Activity Mediated by Monocytes/Macrophages" Retrieved from: download.gsk-clinicalstudyregister.com/files/23093.pdf on May 23, 2012 (2 pages).
Risérus et al., (2008) "Activation of Peroxisome Proliferator-activated Receptor (PPAR) Delta Promotes Reversal of Multiple Metabolic Abnormalities, Reduces Oxidative Stress, and Increases Fatty Acid Oxidation in Moderately Obese Men," Diabetes, 57(NR. 2):332-9.
Ritland et al., (1999) 'Evaluation of 5-Aminosalicylic Acid (5-ASA) for Cancer Chemoprevention: Lack of Efficacy against Nascent Adenomatous Polyps in the Apc$^{Min}$ Mouse,' Clin Cancer Res, 5(4):855-63.
Robertson et al., (1985) 'Structure-Activity Relationships of Arylimidazopyridine Cardiotonics: Discovery and Inotropic Activity of 2-[2-Methoxy-4-(methylsulfinyl)phenyl]-1H-imidazo[4,5-c]pyridine,' J Med Chem, 28(6):717-27.
Rousseaux et al., (2005) "Intestinal Anti-inflammatory Effect of 5-Aminosalicylic Acid is Dependent on Peroxisome Proliferator-Activated Receptor-γ," J Exp Med, 201(8):1205-15.
Rousseaux et al., (2010), 'Preclinical and Toxicological Assessments of the Novel Orally Bioavailable PPAR Ligand GED-0507-34-Levo for the Treatment of Inflammatory Bowel Disease,' Gastroenterology 2010 DDW Abstract Supplement, AGA Abstract #1080, 138(5-Suppl 1):S-157.
Rousseaux et al., (2011) 'Preclinical Evaluation of Intestinal Anti-Inflammatory/Analgesic Properties and Phase I Clinical Trial of a New PPAR Agonist Ged-0507-34-Levo,' Gastroenterology, 140(5):S-515 (Abstract).
Rovner (2009) "An Enzyme Reveals an Unexpected Inclusiveness, Protein Binding: Bacterial Enzyme's Active Site Welcomes Both Enantiomers of a Chiral Molecule at the Same Time," Chem Eng News, Nov. 5, 2009 issue, (2 pages) relieved from http://cen.acs.org/articles/87/web/2009/11/Enzyme-Reveals-Unexpected-Inclusiveness.html?type=paidArticleContent.
Schauber J et al., (2004) 'Histone-Deacetylase Inhibitors Induce the Cathelicidin LL-37 in Gastrointestinal Cells,' Mol Immunol, 41(9):847-54.
Schwab et al., (2007) 'Role of Nuclear Hormone Receptors in Butyrate-Mediated Up-Regulation of the Antimicrobial Peptide Cathelicidin in Epithelial Colorectal Cells,' Mol Immunol, 44(8):2107-14.
Sherwin (1924), "Acetylation as a Physiologic Reaction," Proc Soc Exper Biol & Med, 22:182.
Speca et al., (2012) 'Cellular and Molecular Mechanisms of Intestinal Fibrosis,' World J Gastroenterol, 18(28):3635-61.
Tanaka et al.,(2001) "Ligands for Peroxisome Proliferator-Activated Receptors α and γ Inhibit Chemically Induced Colitis and Formation of Aberrant Crypt Foci in Rats," Cancer Res., 61(6): 2424-8.
Tosti et al., (2009) 'Treatment Strategies for Alopecia,' Expert Opin Pharmacother, 10(6):1017-26.
Troilius A and Troilius C, (1999), 'Hair Removal with a Second Generation Broad Spectrum Intense Pulsed Light Source—A Long Term Follow-up,' J Cutan Laser Ther, 1(3):173-8.
Tuleu, et al., (2002) "Colonic Delivery of 4-Aminosalicylic Acid Using Amylose-Ethyl Cellulose-Coated Hydroxypropyl Methyl Cellulose Capsules," Aliment Pharmacol Ther., 167(10):1771-9.
Tursi et al., (2002), 'Long-Term Treatment with Mesalazine and Rifaximin Versus Rifaximin Alone for Patients with Recurrent Attacks of Acute Diverticulitis of Colon,' Digest Liver Dis, 34(7):510-5.

(56) References Cited

OTHER PUBLICATIONS

Tursi, (2004), 'Acute Diverticulitis of the Colon—Current Medical Therapeutic Management,' Exp Opin Pharmacother, 5(1):55-9.
Tzameli et al., (2004) 'Regulated Production of a Peroxisome Proliferator-Activated Receptor-γ Ligand During an Early Phase of Adipocyte Differentiation in 3T3-L1 Adipocytes,' J Biol Chem, 279(34):36093-102.
Van't Riet, Bart, et al. (1979) "Synthesis of Hydroxy and Amino-Substituted Benzohydroxamic Acids: Inhibition of Ribonucleotide Reductase and Antitumor Activity," J Med Chem, 22(5) 589-92.
Venkatraman et al., (2004) 'Alpha-Lipoic Acid-Based PPARγ Agonists for Treating Inflammatory Skin Diseases,' Arch Dermatol Res, 296(3):97-104 (Abstract).
Wallace et al., (1989) 'Inhibition of Leukotriene Synthesis Markedly Accelerates Healing in Rat Model of Inflammatory Bowel Disease,' Gastroenterology, 96(1):29-36.
Wang et al., (2002) "Further Development and Validation of Emphirical Scoring Functions for Structure-Based Binding Affinity Prediction," J Comput Aided Mol Des, 16(1):11-26.
Wang et al., (2004) 'Cutting Edge: 1,25-Dihydroxyvitamin D3 is a Direct Inducer of Antimicrobial Peptide Gene Expression,' J Immunol, 173(5):2909-12.
Wei et al., (2010) 'Peroxisome Proliferator-Activated Receptor γ: Innate Protection from Excessive Fibrogenesis and Potential therapeutic Target in Systemic Sclerosis,' Curr Opin Rheumatol, 22(6):671-6 (HHS Public Access version of Author Manuscript).
Westin et al., (1998) "Interactions Controlling the Assembly of Nuclear-Receptor Heterodimers and Co-Activators," Nature, 395(6698):199-202.
Williams and Hallett (1989) "Effect of Sulphasalazine and its Active Metabolite, 5-Amino-Salicylic Acid, on Toxic Oxyden Metabolite Production by Neutrophils," Gut, 30(11):1581-7.
Written Opinion of International Searching Authority and and International Search Report issued in PCT/EP2020/051810 dated May 5, 2020 (12 pages).
Written Opinion of the International Searching Authority for International Application No. PCT/EP2008/052354 dated Jun. 9, 2008 (10 pages).
Written Opinion of the International Searching Authority for International Application No. PCT/EP2008/068265 dated Aug. 11, 2009 (12 pages).
Written Opinion of the International Searching Authority for International Application No. PCT/EP2013/052617 dated Aug. 12, 2014 (4 pages).
Written Opinion of the International Searching Authority for International Application No. PCT/EP2013/069062 dated Dec. 10, 2013 (6 pages).
Written Opinion of the International Searching Authority for International Application No. PCT/EP2013/069063 dated Dec. 29, 2013 (7 pages).
Written Opinion of the International Searching Authority for International Application No. PCT/IE2006/000076 dated Feb. 1, 2007 (9 pages).
Wu et al., (2006) 'Effects of Rosiglitazone on Expression of TGF-A1 in Experimental Hepatic Fibrosis Rats,' Chin J Gastroenterol Hepatol, 15(2):126-9.
Xu et al., (2001) "Structural Determinants of Ligand Binding Selectivity Between the Peroxisome Proliferator-Activated Receptors," Proc Natl Acad Sci USA, 98(24):13919-24.
Yanai et al., (2004) "Para-Position Derivatives of Fungal Anthelmintic Cyclodepsipeptides Engineered with Streptomyces Venezuelae Antibiotic Biosynthetic Genes," Nat Biotechnol, 22(7):848-55.
Ye; "Regulation of PPARy function by TNF-a"; 2008; Biochemical and Biophysical Research Communications; 374: 405-408 (Year: 2008).
Youssef and Badr, (2004) "Role of Peroxisome Proliferator-Activated Receptors in Inflammation Control," J Biomed Biotechnol, 2004(3):156-66.
Yu et al., (2010) 'Peroxisome Proliferator-Activated Receptors Gamma Reverses Hepatic Nutritional Fibrosis in Mice and Suppresses Activation of Hepatic Stellate Cells in vitro,' Int J Biochem Cell Biol, 42(6):948-57.
Zhou et al., (1999) 'Intestinal Metabolism and Transport of 5-Aminosalicylate,' Drug Metab Dispos, 27(4):479-85.
Bassaganya-Riera J et al., (2011), 'Activation of PPARγ and δ by Dietary Punicic Acid Ameliorates Intestinal Inflammation in Mice,' Br J Nutr, 106(6):878-86.
Fu Xiaoxia et al. (2010) "Advance on PPARγ and ligands thereof and liver fibrosis," Chinese Journal of Clinical Gastroenterology 22(4):254-256.
Lv Chunhua et al. (2009) "Advance on fibrosis in inflammatory bowel disease," Practical Clinical Medicine 10(2):127-129.
Patricia J. Sime (2007) "Exploring the peroxisome proliferator activated receptor gamma (PPARγ) pathway as a novel thereapy for lung fibrosis," Seminar of Integrated Traditional Chinese and Western Experimental Medicine pp. 36-38.
Written Opinion of International Searching Authority and International Search Report issued in International application No. PCT/EP2020/053369 dated Apr. 20, 2020 (10 pages).

\* cited by examiner

| Metavir score (Activity A0→A3 & Fibrosis F0→F4) | | |
|---|---|---|
| | Activity (Necrosis & inflammation) | Fibrosis |
| 0 | A0 | F0 |
| low | A1 | F1 |
| moderate | A2 | F2 |
| severe | A3 | F3 |
| Cirrhosis | | F4 |

METHODS OF TREATING FIBROSIS

This application is a continuation of U.S. Ser. No. 15/593,864, filed May 12, 2017, which is a divisional of U.S. Ser. No. 14/377,362, filed Aug. 7, 2014, which is the U.S. national stage of International (PCT) Patent Application No. PCT/EP2013/052617, filed Feb. 8, 2013, and published under PCT Article 21(2) in English, which claims priority to EP12425027.5, filed Feb. 9, 2012, and U.S. Ser. No. 61/644,544, filed May 9, 2012, each of which is incorporated by reference in its entirety.

SEQUENCE LISTING

The instant application contains a Sequence Listing which has been submitted in electronically in text format and is hereby incorporated by reference in its entirety. Said text copy, created on May 21, 2013, is named PS966PCT_SL.txt and is 3,284 bytes in size.

BACKGROUND

Fibrosis is the formation of excess fibrous connective tissue in an organ or tissue in a reparative or reactive process, e.g., healing, usually because of injury or long-term inflammation. Fibrosis causes the affected tissues to harden and/or swell and reduces the flow of fluids through these tissues. As result, tissues with fibrosis may not be able to function properly.

For example, hepatic fibrosis can be described as the wound-healing response to chronic hepatic injury as a result of, for example, alcohol and/or drug abuse, viral and parasitic infection (e.g., hepatitis such as hepatitis B or C), nonalcoholic steatohepatitis (NASH), iron and copper overload, and autoimmune diseases. All chronic liver diseases can lead to liver fibrosis with the principle causes chronic viral hepatitis B and alcoholic liver disease. The hepatic endocannabinoid system mediates both pro- and anti-fibrogenic effects by activating distinct signaling pathways that differentially effect proliferation and death of fibrogenic cell types. Over time this process can result in cirrhosis of the liver in which the architectural organization of the functional units of the liver becomes so disrupted that blood flow through the liver and liver function become disrupted.

Liver fibrosis represents a common and difficult challenge of worldwide importance. At present, the only curative treatment for end stage cirrhosis is transplantation, but even in the developed world, the number of donor organs available and the clinical condition of the potential recipient limit the applicability of this technique. The development of fibrosis, and particularly cirrhosis, is associated with a significant morbidity and mortality. Thus, there is a considerable imperative to develop antifibrotic strategies that are applicable to liver fibrosis.

Renal fibrosis causes significant morbidity and mortality as the primary acquired lesion leading to the need for dialysis or kidney transplantation. Fibrosis can occur in either the filtering or reabsorptive component of the nephron, the functional unit of the kidney. Fibrosis can also occur in the heart, e.g., cardiac fibrosis can occur as a thickening of a heart valve.

Intestinal fibrosis is a common complication of inflammatory bowel disease (IBD) that can become symptomatic and may require surgical intervention if stricture formation ensues. Most of the traditional and novel mechanisms underlying intestinal fibrosis are associated with chronic inflammation.

SUMMARY

Provided herein, for example, are methods for treating fibrosis comprising administering compounds disclosed herein to a patient. Compound for use in such methods are also provided. For example, a method of preventing or treating hepatic fibrosis and/or intestinal fibrosis in a subject or patient in need thereof or suffering from same is provided, comprising administering a therapeutically and/or pharmaceutically acceptable amount of a compound represented by

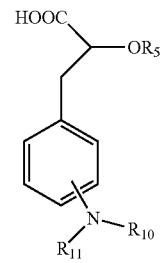

wherein $R_{10}$ is selected from the group consisting of H and $C_1$-$C_6$alkyl;

$R_{11}$ is selected from the group consisting of H, $C_1$-$C_6$alkyl, and —C(O)—$C_1$-$C_6$alkyl;

$R_5$ is $C_1$-$C_6$alkyl; and pharmaceutically acceptable salts thereof.

Suitably, in some embodiments, $R_5$ can be H.

Suitably, the $C_1$-$C_6$alkyl functionalities of $R_{10}$, $R_{11}$ and/or $R_5$ may be independently selected from the group consisting of: methyl, ethyl, propyl, pentyl and hexyl. The alkyl functionality may be linear or branched. Methyl and ethyl alkyl functionalities are particularly preferred with methyl being the most preferred alkyl functionality.

Suitably, the nitrogen may be attached to the ring at the 2', 3', 4' or 5' positions. Preferably, the nitrogen is attached at the 3' or 4' position. The 4' position is most preferred.

Exemplary contemplated compounds may include formulas A' and A", wherein $R_{10}$, $R_{11}$ and $R_5$ are provided above and herein:

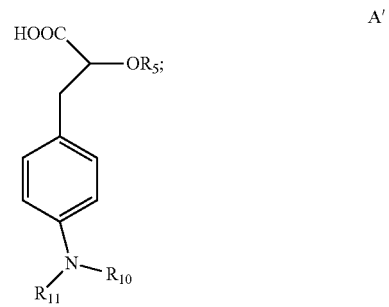

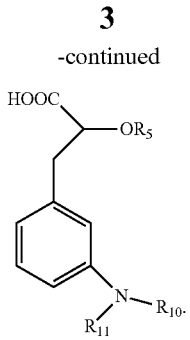

Suitably, in some embodiments, $R_5$ can be H.

Suitably, the $C_1$-$C_6$alkyl functionalities of $R_{10}$, $R_{11}$ and/or $R_5$ may be independently selected from the group consisting of: methyl, ethyl, propyl, pentyl and hexyl. The alkyl functionality may be linear or branched. Methyl and ethyl alkyl functionalities are particularly preferred with methyl being the most preferred alkyl functionality. In certain embodiments, $R_5$ is methyl, ethyl, propyl or is e.g., methyl. In certain embodiments, $R_5$ is methyl, ethyl, propyl or is e.g., methyl.

Also provided herein is a method of preventing or treating hepatic or intestinal fibrosis, comprising administering to a patient in need thereof, a pharmaceutical preparation comprising a PPARγ agent such as a compound disclosed herein. Contemplated herein are methods of preventing or treating renal fibrosis, cardiac fibrosis, endomyocardial fibrosis, idiopathic pulmonary fibrosis, myelofibrosis, retroperitoneal fibrosis, and/or nephrogenic systemic fibrosis, comprising administering to a patient in need thereof, a pharmaceutical preparation comprising a PPARγ agent such as a compound disclosed herein. For example, methods disclosed herein may include methods wherein the patient is human. Accordingly, the compounds described herein may be used in the treatment and/or prevention of these diseases/conditions.

These and other aspects and advantages of the disclosure will become apparent upon consideration of the following figures, detailed description, and claims.

BRIEF DESCRIPTION OF THE DRAWINGS

FIG. 12 depicts microscopic findings of colons from DSS and DSS+GED mice chronic colitis. Colon tissues were fixed in 4% PFA and transversal sections (4 μm) were stained with May-Grunwald-Giemsa (H&E) and Masson's trichrome. DSS mice showed severe inflammatory degree and fibrosis both in submucosa and serosa compared to controls, while GED treatment determined the restoring of normal intestinal wall architecture. Data are expressed as mean±SEM; *=$p<0.05$; =$p<0.01$ and *=$p<0,005$ vs $H_2O$.

DETAILED DESCRIPTION

Figure 1:
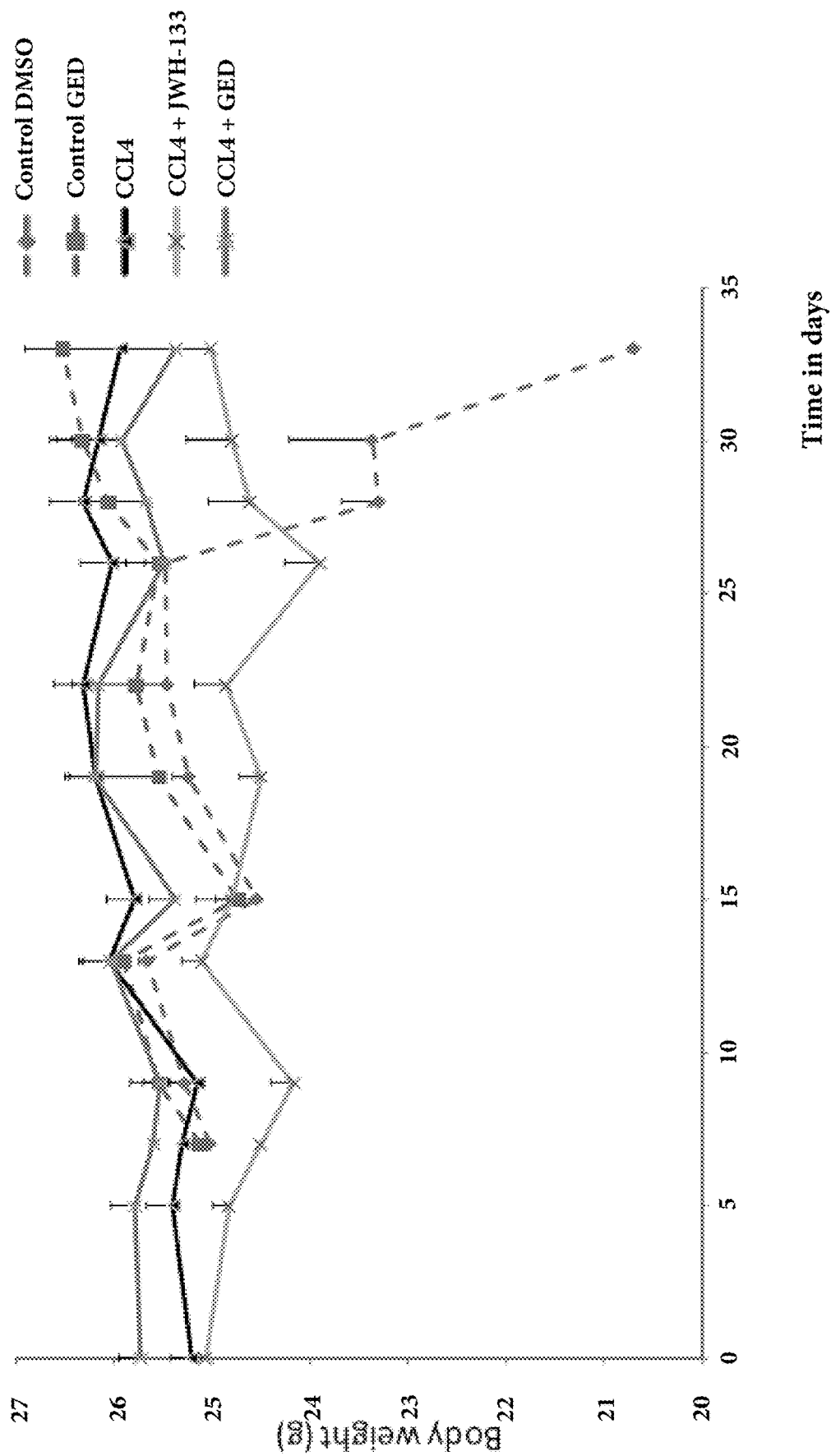
FIG. 1 depicts the body weight evolution of mice upon administration of $CCl_4$, JWH-133 and compound 34.

The disclosure is based, in part, upon the discovery that certain compounds disclosed herein have the ability to prevent or treat fibrosis, for example, in the liver or in the colon. In one aspect, the disclosure is directed to methods of preventing or treating fibrosis, e.g. hepatic fibrosis and/or intestinal fibrosis, in patients in need thereof. The disclosed methods comprise administering a compound disclosed herein.

Before further description, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

A "patient," "subject" or "host" to be treated by the subject method may mean either a human or non-human animal, e.g. a small mammal such as a mouse or rat, and including horse, cow, dog, cat, etc.

The term "therapeutic agent" is art-recognized and refers to any chemical moiety that is a biologically, physiologically, or pharmacologically active substance that acts locally and/or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The term "therapeutic effect" is art-recognized and refers to a local and/or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The term "treating" is art-recognized and refers to curing as well as ameliorating at least one symptom of any condition or disease.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer, e.g. from 1 to 6 carbons. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The definition of each expression, e.g. alkyl, m, n, and the like, when it occurs more than once in any structure, is intended to be independent of its definition elsewhere in the same structure.

Certain compounds contained in compositions of the present invention may exist in particular geometric or stereoisomeric forms. In addition, compounds of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67$^{th}$ Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Compounds

Compounds contemplated for use in one or more of the disclosed methods include compounds represented by formula I, or a pharmaceutically acceptable salt, enantiomer or stereoisomer thereof:

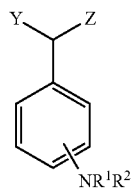

(I)

wherein:
$R^1$ and $R^2$ are each independently selected from the group consisting of H and $C_{1-6}$ alkyl; or $R^1$ and $R^2$ may be taken together with the nitrogen atom to which they are attached to form an aromatic or aliphatic ring with 5 or 6 atoms;
Y and Z are independently selected from the group consisting of H, OH, COOH, —$OR^3$, —$CH(OR_3)$ COOH; and
$R^3$ is selected from the group consisting of H, phenyl, benzyl, vinyl, allyl, $C_{1-6}$ alkyl or $C_{1-6}$ alkyl substituted by one or more halogens; or a pharmaceutically acceptable salt thereof.

Suitably, the $C_1$-$C_6$alkyl functionalities may be independently selected from the group consisting of: methyl, ethyl, propyl, pentyl and hexyl. The alkyl functionality may be linear or branched. Methyl and ethyl alkyl functionalities are particularly preferred with methyl being the most preferred alkyl functionality.

In an embodiment, Y may be H or COOH. For example, Y may be H and Z may be $CH(OR^3)COOH$, or Y may be COOH and Z maybe —$OR^3$. In some embodiments, $R^3$ may be methyl, ethyl, n-propyl, or isopropyl.

In other embodiments, the $NR^1R^2$ moiety of Formula I may be in the 4' position or may be in the 3' position. In certain embodiments, $R^1$ and $R^2$ are H.

Suitably, in some embodiments, $R_3$ can be H.

Exemplary compounds also include those represented by formulas IIa or IIb or a pharmaceutically acceptable salt, enantiomer or stereoisomer of:

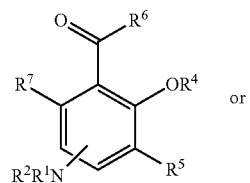

(IIa)

or

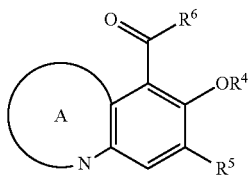

(IIb)

wherein:
$R^1$ and $R^2$ are independently selected from the group consisting of H and $C_{1-6}$ alkyl; or $R^1$ and $R^2$ may be taken together with the nitrogen atom to which they are attached to form an aromatic or aliphatic ring with 5 or 6 atoms;
$R^6$ is selected from the group consisting of —$NR^9OH$, OH, and —$OR^9$;
$R^9$ is $C_{1-6}$ alkyl;
$R^4$ is selected from the group consisting of H, halo, phenyl, benzyl, vinyl, allyl, $C_{1-6}$ alkyl and $C_{1-6}$ alkyl substituted by one or more halogens;
$R^5$ and $R^7$ are independently selected from the group consisting of hydrogen or halo, or
$R^4$ and $R^5$, or $R^4$ and $R^6$ together, form a fused heterocyclic ring with 5 or 6 atoms, optionally substituted with halo or $C_{1-6}$ alkyl; and
A is a fused heterocyclic ring; or a pharmaceutically acceptable salt thereof.

Suitably, the $C_1$-$C_6$alkyl functionalities may be independently selected from the group consisting of: methyl, ethyl, propyl, pentyl and hexyl. The alkyl functionality may be linear or branched. Methyl and ethyl alkyl functionalities are particularly preferred with methyl being the most preferred alkyl functionality.

In certain embodiments, the $NR^1R^2$ moiety of formula IIa may be in the 4' position or may be in the 3' position. In certain embodiments, $R^1$ and $R^2$ are H. $R^9$ in some embodiments, may be methyl, ethyl, n-propyl, or isopropyl.

In some embodiments a contemplated compound can be represented by

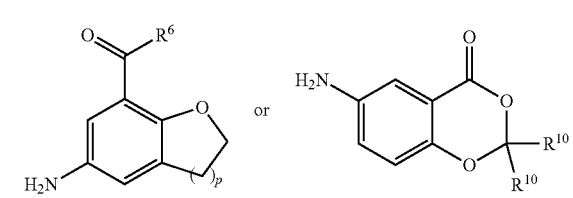

wherein p is 1 or 2;
$R^6$ is selected from the group consisting of OH or —$OR^9$, wherein $R^9$ is defined above; and
$R^{10}$ is selected independently for each occurrence from the group consisting of H, halo, or $C_{1-6}$ alkyl, e.g., methyl or ethyl.

The disclosure also provides, at least in part, compounds represented by the formulas depicted below, for use in the disclosed methods.

For example, contemplated herein for use in disclosed methods are compounds of formula III:

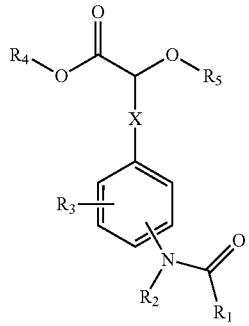

III wherein X is $C_1$-$C_3$alkylene, optionally substituted with one, two or three substituents selected from halogen or hydroxyl;
$R_1$ is selected from the group consisting of $C_1$-$C_6$alkyl, $C_3$-$C_6$cycloalkyl, $C_2$-$C_6$alkenyl, and $C_2$-$C_6$alkynyl;
$R_2$ is selected from the group consisting of hydrogen and $C_1$-$C_6$alkyl;
$R_3$ is independently selected, for each occurrence from the group consisting of hydrogen, $C_1$-$C_6$alkoxy, $C_1$-$C_6$alkyl, cyano, $C_3$-$C_6$cycloalkyl, halogen, hydroxyl, and nitro;
$R_4$ is selected from the group consisting of hydrogen and $C_1$-$C_6$alkyl;
$R_5$ is $C_1$-$C_6$alkyl;
or pharmaceutically acceptable salts or N-oxides thereof.
Suitably, in some embodiments, $R_5$ can be H.
Suitably, the $C_1$-$C_6$alkyl functionalities may be independently selected from the group consisting of: methyl, ethyl, propyl, pentyl and hexyl. The alkyl functionality may be linear or branched. Methyl and ethyl alkyl functionalities are particularly preferred with methyl being the most preferred alkyl functionality.
In one embodiment, $R_1$ of formula III can be $C_1$-$C_6$alkyl, such as methyl. In one embodiment, $R_2$ can be hydrogen. In another embodiment, $R_3$ can be selected from the group consisting of hydrogen, $C_1$-$C_6$alkyl, halogen, and hydroxyl. In a further embodiment, $R_3$ can be hydrogen. In one embodiment, $R_4$ and $R_5$ can each be $C_1$-$C_6$alkyl. In another embodiment, $R_4$ may be hydrogen and $R_5$ may be methyl. In one embodiment, X may be $(CH_2)_n$, wherein n is 1 or 2, such as 1.
In another embodiment, the moiety —$NR_2$—$COR_1$ of formula III can be in the meta or the para position relative to X as shown in formulas IIIa and IIIb.

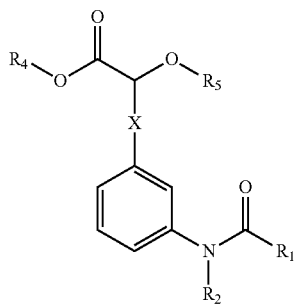

IIIa

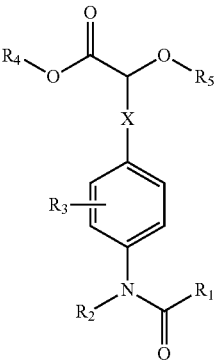

IIIb

The disclosure also provides compounds represented by formula IV, as depicted below, which may be used in the disclosed methods, e.g.:

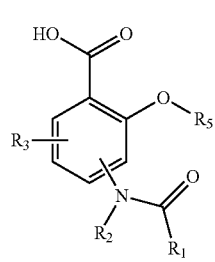

IV wherein $R_1$ is selected from the group consisting of $C_1$-$C_6$alkyl, $C_3$-$C_6$cycloalkyl, $C_2$-$C_6$alkenyl, and $C_2$-$C_6$alkynyl;
$R_2$ is selected from the group consisting of hydrogen and $C_1$-$C_6$alkyl;
$R_3$ is independently selected, for each occurrence from the group consisting of hydrogen, $C_1$-$C_6$alkoxy, $C_1$-$C_6$alkyl, cyano, $C_3$-$C_6$cycloalkyl, halogen, hydroxyl, and nitro;
$R_5$ is hydrogen or $C_1$-$C_6$alkyl;
or pharmaceutically acceptable salts or N-oxides thereof.
Compounds of Formula V are also contemplated as shown below:

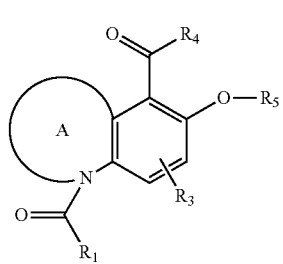

V wherein $R_1$ is selected from the group consisting of $C_1$-$C_6$alkyl, $C_3$-$C_6$cycloalkyl, $C_2$-$C_6$alkenyl, and $C_2$-$C_6$alkynyl;
$R_3$ is independently selected, for each occurrence from the group consisting of hydrogen, $C_1$-$C_6$alkoxy, $C_1$-$C_6$alkyl, cyano, $C_3$-$C_6$cycloalkyl, halogen, hydroxyl, and nitro;

$R_4$ is selected from the group consisting of hydrogen and $C_1$-$C_6$alkyl;

$R_5$ is hydrogen or $C_1$-$C_6$alkyl; and

A is a fused five or six membered heterocycle;

or pharmaceutically acceptable salts or N-oxides thereof.

In one embodiment, $R_1$ can be $C_1$-$C_6$alkyl, such as methyl. In another embodiment, $R_1$ and $R_3$ can each be $C_1$-$C_6$alkyl, such as methyl. In one embodiment, $R_2$ can be hydrogen.

In some embodiments, a compound can be represented by

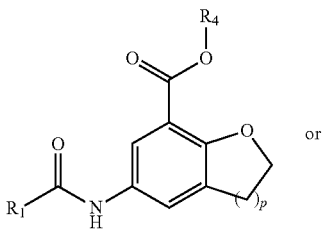

or

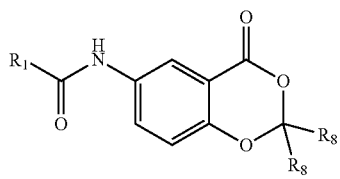

wherein p is 1 or 2;

$R_1$ is selected from the group consisting of $C_1$-$C_6$alkyl, $C_3$-$C_6$cycloalkyl, $C_2$-$C_6$alkenyl, and $C_2$-$C_6$alkynyl;

$R_4$ and $R_8$ are each independently selected from the group consisting of hydrogen and $C_1$-$C_6$alkyl;

or pharmaceutically acceptable salts or N-oxides thereof.

For example, in one embodiment, contemplated compounds for use in disclosed methods include compounds of formula A:

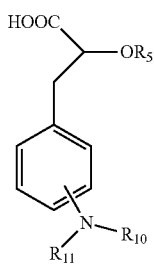

$R_{10}$ is selected from the group consisting of H and $C_1$-$C_6$alkyl (e.g. methyl);

$R_{11}$ is selected from the group consisting of H, $C_1$-$C_6$alkyl, and —C(O)—$C_1$-$C_6$alkyl; (e.g., $R_{11}$ may be H, methyl, —C(O)-methyl, or —C(O)-ethyl).

$R_5$ is $C_1$-$C_6$alkyl (e.g., $R_5$ may be methyl, ethyl, or propyl);

or pharmaceutically acceptable salts or N-oxides thereof.

For example, contemplated herein for use in disclosed methods are formulas A' and A":

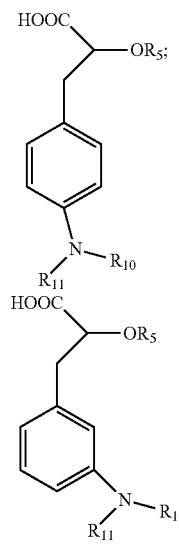

Exemplary compounds contemplated herein for use in disclosed methods include:

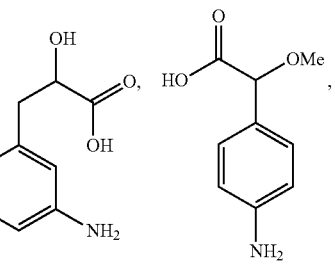

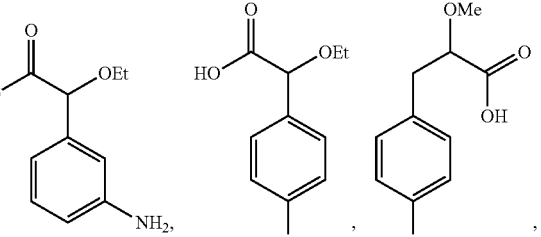

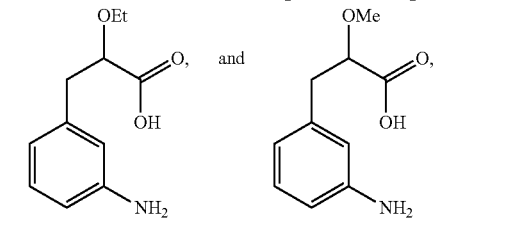

or a pharmaceutically acceptable salt thereof.

In some embodiments, contemplated compounds include: 4-amino-N-hydroxy-2-methoxybenzamide (compound 13); 6-methoxy quinoline-5-carboxylic acid (compound 36); 6-methoxy-1,2,3,4-tetrahydroquinoline-5-carboxylic acid (compound 37); and 5-diisopropylaminosalicylic acid (compound 38).

Other exemplary compounds include those represented by:

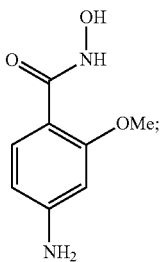
(compound 13)

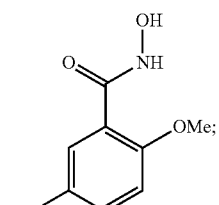
(compound 14)

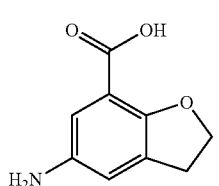
(compound 26)

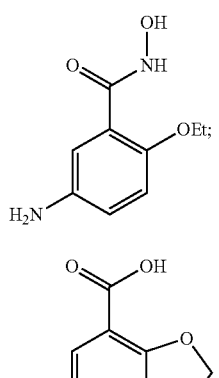
(compound 17)

(compound 31)

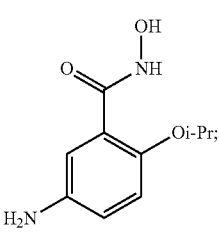
(compound 28)

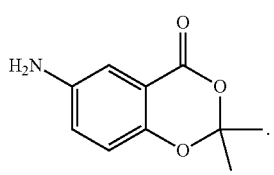

Compounds contemplated herein include racemic mixtures, and enantiomers of compounds, for example: (±)-2-hydroxy-3-(3'-aminophenyl) propionic acid (compound 20); (±)-2-methoxy-2-(4'-aminophenyl) acetic acid (compound 23); (±)-2-ethoxy-2-(3'-aminophenyl) acetic acid (compound 32); (±)-2-ethoxy-2-(4'-aminophenyl) acetic acid (compound 33); (±)-2-methoxy-3-(4'-aminophenyl) propionic acid (compound 34) "±34" (racemic form); (±)-2-ethoxy-3-(4'-aminophenyl) propionic acid (compound 39); (±)-2-ethoxy-3-(3'-aminophenyl) propionic acid (compound 40).

For example, the compounds used in the methods disclosed herein can be enantiomers of the following racemic mixtures: (R,S)-2-hydroxy-2-(3-aminophenyl)acetic acid (compound 10); (R,S)-2-hydroxy-2-(4-aminophenyl)acetic acid (compound 11); (R,S)-2-hydroxy-3-(4'-aminophenyl) propionic acid (compound 21); (R,S)-2-methoxy-2-(3'-aminophenyl)acetic acid (compound 22); (R,S)-2-methoxy-3-(3'-aminophenyl)propionic acid (compound 35); (R,S)-2-methoxy-3-(4-aminophenyl)propionic acid (compound 34), as well as enantiomers, e.g.: (+) 2-S-methoxy-3-(4-aminophenyl)propionic acid; (−) 2-R-methoxy-3-(4-aminophenyl) propionic acid. In some embodiments, (R,S)-2-hydroxy-3-(4'-aminophenyl)propionic acid (compound 21) or (±)-2-hydroxy-3-(3'-aminophenyl) propionic acid (compound 20) are preferred.

Other racemic type mixtures of compounds contemplated include: e.g. (±)-2-hydroxy-2-(3'-aminophenyl)acetic acid (compound 10); (±)-2-hydroxy-2-(4'-aminophenyl)acetic acid (compound 11); (±)-2-hydroxy-3-(4'-aminophenyl)propionic acid (compound 21) and (±)-2-methoxy-2-(3'-aminophenyl)acetic acid (compound 22).

Further compounds contemplated for use in the disclosed methods: 5-aminosalicylo-hydroxamic acid (compound 5); 3-dimethylaminosalicylic acid (compound 6); 2-methoxy-4-aminobenzoic acid (compound 7); 2-methoxy-5-aminobenzoic acid (compound 8); 5-methylaminosalicylic acid (compound 9); 4-methylaminosalicylic acid (compound 12); 4-acetylaminosalicylic acid (compound 16); 2-ethoxy-4-aminobenzoic acid (compound 18); 2-ethoxy-5-aminobenzoic acid (compound 19); 4-dimethylaminosalicylic acid (compound 24); 2-ethoxy-4-aminobenzoylhydroxamic acid (compound 25); 6-hydroxyquinoline-5-carboxylic acid (compound 27); 2-(2-propyl)oxy-4-aminobenzoic acid (compound 30); 4-(1-piperazinyl)salicylic acid (compound 41); (R,S) 5-oxa-quinoline-6-carboxylic acid (compound 15); 6-methoxy quinoline-5-carboxylic acid (compound 36); 6-methoxy-1,2,3,4-tetrahydroquinoline-5-carboxylic acid (compound 37); 5-diisopropylaminosalicylic acid (compound 38); and 4-diisopropylaminosalicylic acid (compound 42).

Contemplated compounds, and pharmaceutical compositions, comprising at least one compound, may be selected from the group consisting of: N-acetyl-(R)-(−)-3-(4-aminophenyl)-2-methoxypropionic acid, N-acetyl-(S)-(−)-3-(4-aminophenyl)-2-methoxypropionic acid; and racemic N-acetyl-(S)-(−)-3-(4-aminophenyl)-2-methoxypropionic acid, or a compound selected from:

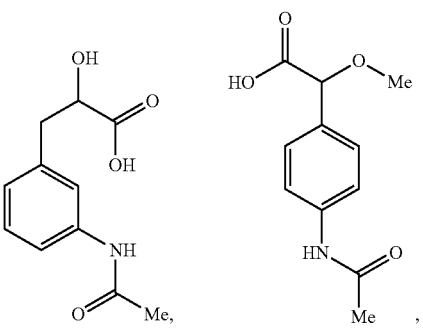

15

-continued

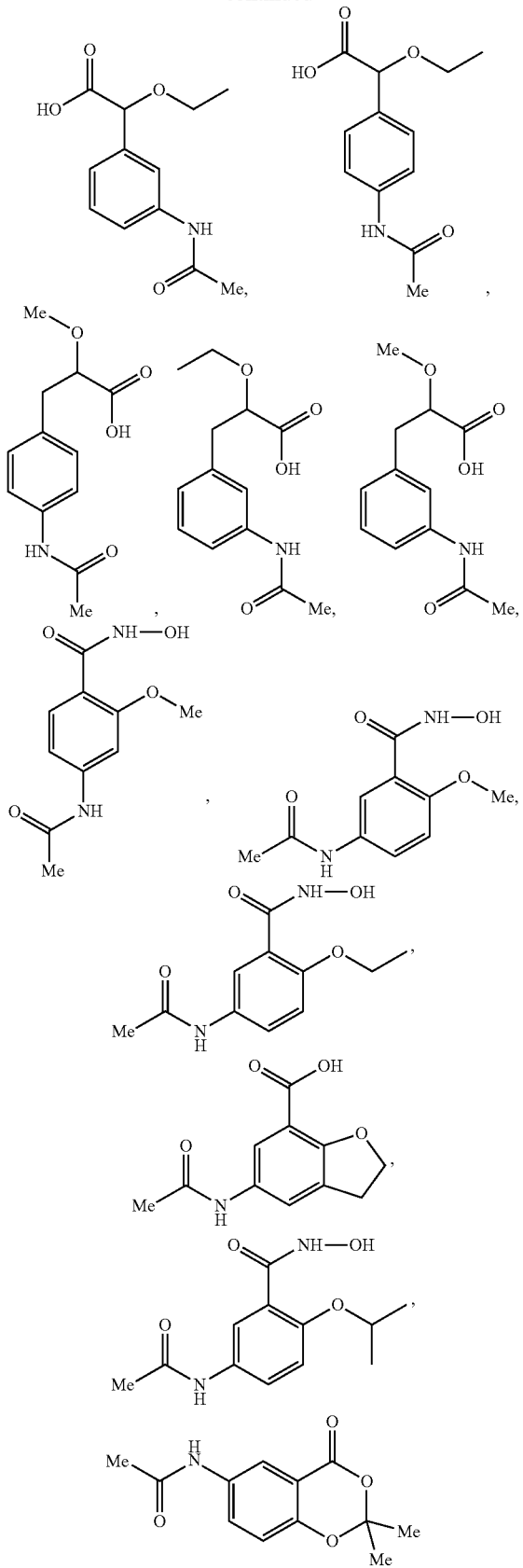

or pharmaceutically acceptable salts or N-oxides thereof.

16

Other contemplated compounds include compound 20, compound 21, 4-acetamino-N-hydroxy-2-methoxybenzamide; 1-acetyl-6-methoxy-1,2,3,4-tetrahydroquinoline-5-carboxylic acid, 5-acetamido-2hydroxybenzoic acid (e.g., acetalyated 5-aminosalicyclic acid) or pharmaceutically acceptable salts or N-oxides thereof.

Also contemplated herein for use in the disclosed methods are compositions that include a compound represented by the depicted formulas and e.g., a pharmaceutically acceptable carrier.

Methods for making contemplated compounds may be found for example in WO2007/010516 and WO2007/010514, each hereby incorporated by reference in their entirety.

Methods

Methods of preventing or treating fibrosis, such as hepatic fibrosis and/or intestinal fibrosis, form part of this disclosure. Such methods may comprise administering to a patient in need thereof or a patient at risk, a pharmaceutical preparation comprising a PPARγ agent such as a compound disclosed herein, e.g., Formulas I, IIa, or IIb, e.g., compounds 17, 29, 34 or 39. For example, a method of preventing or treating hepatic fibrosis is provided comprising administering to a patient in need thereof a compound disclosed herein. Alternatively, a method of preventing or treating intestinal fibrosis is provided comprising administering to a patient in need thereof a compound disclosed herein.

Patients treated using an above method may or may not have detectable fibrosis. In some embodiments, the patient has at least about a 5%, 10%, 20%, 30%, 40% or even 50% or more reduction in the amount of fibrosis present in the patient after administering a disclosed compound, e.g., compounds 17, 29, 34 or 39, after e.g. 1 day, 2 days, 1 week, 1 month or 6 months or more. Administering such a compound may be on, e.g., at least a daily basis. The compound may be administered orally. The delay of clinical manifestation of fibrosis in a patient as a consequence of administering a compound disclosed here may be at least e.g., 6 months, 1 year, 18 months or even 2 years or more as compared to a patient who is not administered a compound such as one disclosed herein.

A patient in need may have hepatic fibrosis that has developed into cirrhosis. A patient at risk of hepatic fibrosis may include those patients with hepatitis B, hepatitis C or nonalcoholic steatohepatitis (NASH). NASH is included in the spectrum of nonalcoholic fatty liver diseases, including steatosis and cirrhosis. NASH is a component of the metabolic syndrome, which is characterized by obesity, type 2 diabetes mellitus, and dyslipidemia, and can eventually lead to hepatocellular carcinoma.

Methods of treating disorders associated with hepatic fibrosis are also provided, such as the treatment of at least one of: certain storage diseases and inborn errors of metabolism, such as, alpha 1-antitrypsin deficiency, copper storage diseases (e.g., Wilson's disease), fructosemia, galactosemia, glycogen storage diseases (e.g., Types III, IV, VI, IX and X), iron-overload syndromes (e.g., hemochromatosis), lipid abnormalities (e.g. Gaucher's disease), peroxisomal disorders (e.g., Zellweger syndrome), and tyrosinemia; bacterial infections (e.g., brucellosis); parasitic infections (e.g., echinococcosis); NASH; viral infections (e.g., hepatitis B or hepatitis C, including chronic hepatitis B or C); Budd-Chiari syndrome; heart failure; hepatic veno-occlusive disease; and portal vein thrombosis. Methods of treating congenital hepatic fibrosis are also contemplated. The composition may be administered orally.

Abuse of drugs and/or alcohol has been implicated in cases of hepatic fibrosis. Contemplated herein are methods of treating hepatic fibrosis in a patient with a history of drug and/or alcohol abuse. For example, a patient with a history of abusing at least one of the following: alcohol, amiodarone, chlorpromazine, isoniazid, methotrexate, methyldopa, oxyphenisatin and, tolbutamide.

A patient at risk of intestinal fibrosis may include those patients with ulcerative colitis, inflammatory bowel disease, or Crohn's disease. A patient at risk may also include those patients with an early age at diagnosis of Crohn's or colitis, extensive and/or severe of colonic disease, patients with the presence of primary sclerosing cholangitis, and/or patient's having a family history of cancer.

Methods of treating disorders associated with intestinal fibrosis are also provided, such as the treatment of at least one of: ulcerative colitis, inflammatory bowel disease, or Crohn's disease.

Contemplated herein are methods of preventing or treating renal fibrosis, cardiac fibrosis, endomyocardial fibrosis, idiopathic pulmonary fibrosis, myelofibrosis, retroperitoneal fibrosis, or nephrogenic systemic fibrosis, comprising administering to a patient in need thereof, a pharmaceutical preparation comprising a PPARγ D agent such as a compound disclosed herein.

The compounds of the invention can be used alone or in combination with each other where by at least two compounds of the invention are used together in a single composition or as part of a treatment regimen. The compounds of the invention may also be used in combination with other drugs for treating drug and/or alcohol abuse, renal fibrosis, cardiac fibrosis, endomyocardial fibrosis, idiopathic pulmonary fibrosis, myelofibrosis, retroperitoneal fibrosis, or nephrogenic systemic fibrosis, drug and/or alcohol abuse.

Generally, a therapeutically effective amount of active component will be in the range of from about 0.1 mg/kg to about 100 mg/kg, optionally from about 1 mg/kg to about 100 mg/kg, optionally from about 1 mg/kg to 10 mg/kg. The amount administered will depend on variables such as the type and extent of disease or indication to be treated, the overall health status of the particular patient, the relative biological efficacy of the binding protein delivered, the formulation of the binding protein, the presence and types of excipients in the formulation, and the route of administration. The initial dosage administered may be increased beyond the upper level in order to rapidly achieve the desired blood-level or tissue level, or the initial dosage may be smaller than the optimum and the daily dosage may be progressively increased during the course of treatment depending on the particular situation. Human dosage can be optimized, e.g., in a conventional Phase I dose escalation study designed to run from 0.5 mg/kg to 20 mg/kg. Dosing frequency can vary, depending on factors such as route of administration, dosage amount and the disease condition being treated. Exemplary dosing frequencies are once per day, once per week and once every two weeks.

Contemplated formulations or compositions comprise a disclosed compound and typically include a pharmaceutically acceptable carrier.

Compositions contemplated herein may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, film-coated tablets, sugar-coated tablets, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

Formulations and compositions may include micronized crystals of the disclosed compounds. Micronization may be performed on crystals of the compounds alone, or on a mixture of crystals and a part or whole of pharmaceutical excipients or carriers. Mean particle size of micronized crystals of a disclosed compound may be for example about 5 to about 200 microns, or about 10 to about 110 microns.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as film coated tablets or sugar coated tablets, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal or topical administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants. The efficacy of treatment with the subject compositions may be determined in a number of fashions known to those of skill in the art.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Except where indicated otherwise, the order of steps or order for performing certain actions are immaterial so long as the invention remains operable. Moreover, unless otherwise noted, two or more steps or actions may be conducted simultaneously.

EXAMPLES

The disclosure is further illustrated by the following examples. The following examples are provided for illustration purposes only, and are not to be construed as limiting the scope or content of the disclosure in any way.

Example 1: Liver Fibrosis Study

Liver fibrosis was induced in Male C57bl6 mice (Charles River, l'Arbresle, France) by injection of carbon tetrachloride ($CCl_4$). The C57bl6 mice weighed 22-25 g and were maintained in laboratory conditions for 1 week before experiment. Animals were housed 5 per cage with food and water available ad libitum.

The study consisted of 5 test groups (see Table 1): control gavage (CG), control intraperitoneal (CIP), carbon tetrachloride ($CCl_4$), compound 34 and JWH-133 agent (see Julien et al., (2005) *Gastroenterology* 128: 742-755 (for JWH-133, a CB2-specific agonist and anti-fibrogenic agent)).

TABLE 1

| Test Group | Treatment | Dose Schedule |
|---|---|---|
| control oral gavage (5 mice) | Carboxymethylcellulose solution (oral gavage vehicle) and olive oil ($CCl_4$ vehicle) | Daily for >5 weeks |
| control intraperitoneal (5 mice) | DMSO/Tween (JWH-133 vehicle) and olive oil ($CCl_4$ vehicle) | Daily for >5 weeks |
| carbon tetrachloride (10 mice) | $CCl_4$ in olive oil via intraperitoneal administration (200 uL) | 3 times a week (every two days) for >5 weeks |
| compound 34 (10 mice) | 30 mM solution of compound 34 in 0.5% CMC administered via oral gavage (200 uL) and $CCl_4$ in olive oil via intraperitoneal administration (200 uL) | 34: Daily for >5 weeks $CCl_4$: 3 times a week for >5 weeks |
| JWH-133 agent (10 mice) | 3 mg/kg of JWH-133 in DMSO/Tween via intraperitoneal administration (100 uL) and CCl4 in olive oil via intraperitoneal administration (200 uL) | JWH: Daily for >5 weeks $CCl_4$: 3 times a week for >5 weeks |

The effectiveness of compound 34 (specific ligand of PPARg) as compared to JWH-133 (anti-fibrogenic agent) was evaluated. Compound 34 was administered orally in combination with $CCl_4$ injections for ca. 5 weeks. Compound 34 was dosed daily at 200 uL of a 30 mM solution. JWH-133 was administered daily via intraperitoneal injections at 3 mg/kg (dose volume=100 uL). The model of liver fibrosis is induced by chronic exposure to increased dosages of $CCl_4$ for 5 weeks. The first week, mice received an intraperitoneal injection of $CCl_4$, resuspended in olive oil, at the dosage of 80 µl/kg of mice body weight twice a week. At week 2, 3 injections of $CCl_4$ at the dosage of 160 µl/kg were performed every two days. At week 3, 3 injections of $CCl_4$ at the dosage of 240 µl/kg were performed every two days. At week 4, 3 injections of $CCl_4$ at the dosage of 320 µl/kg were performed every two days. Mice were euthanized, at week 5, 3 days after the last $CCl_4$ administration.

Body weights were recorded for the duration of the experiment. As seen in FIG. 1, there was no detected difference in the body weight evolution between the different groups of mice.

Livers were excised and aliquots were snap frozen in liquid nitrogen and kept at −80° C. until analyzed. A portion of each liver part was fixed in 10% formalin for histology.

Example 2: Histology Analysis of Liver Fibrosis Study

Figure 2A:
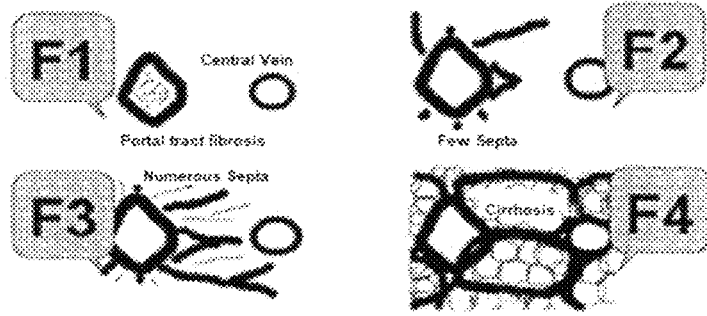
FIG. 2A depicts an explanation of metavir scores and FIG. 2B depicts the effect of $CCl_4$, JWH-133+$CCl_4$ and compound 34+$CCl_4$ on the liver and specifies a metavir score for each group.
Figure 2B:
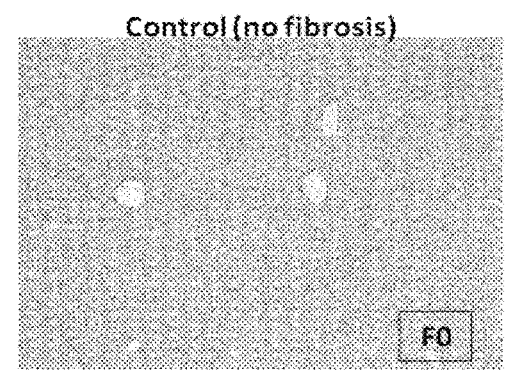
Figure 2B:
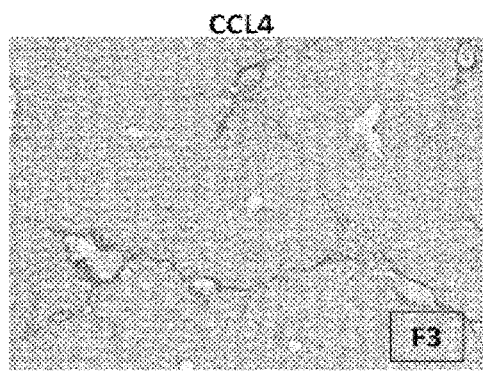
Figure 2B:
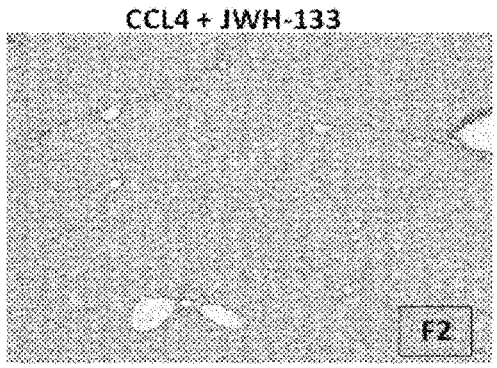
Figure 2B:
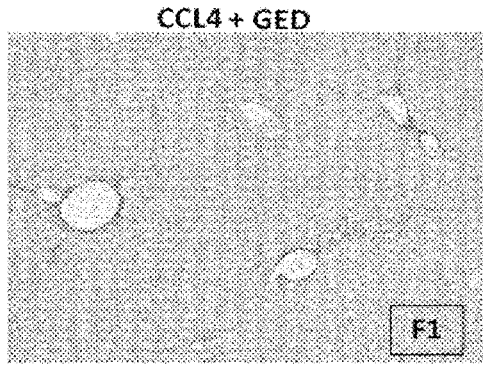

The formalin-fixed liver tissue was processed and 5 m thick paraffin sections were stained with hematoxylin and eosin (H&E) and Picrosirius red staining (specific coloration for collagen in tissue sections) to evaluate the degree of fibrosis in the liver. Each section was analyzed blindly by 3 different experimenters for the quantification of the degree of fibrosis for each lobe of the liver (5) using the Metavir score (see FIG. 2A for Metavir Score chart). The photographs seen in FIG. 2B were obtained with a 20× objective. The control group had a F0 score and the $CCl_4$ group had a F3 score, indicating fibrosis of the liver. Compound 34 (GED) showed a greater reduction in fibrosis than the JWH-133 group with respective scores of F1 for Compound 34 and F2 for JWH-133.

Figure 3A:
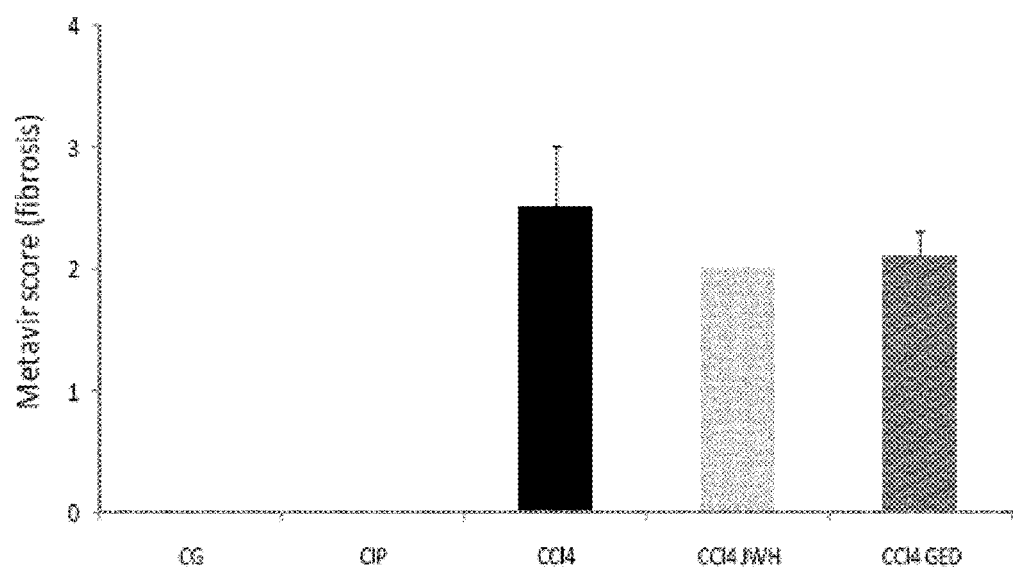
FIG. 3A depicts the metavir score and FIG. 3B adapted metavir score of livers from mice subjected to $CCl_4$, JWH-133+$CCl_4$ and compound 34+$CCl_4$.

As expected, no fibrosis was observed in the two groups of control mice (Control gavage (CG) and Control IP (CIP)). In the group of fibrotic mice (CCl4 group) receiving only vehicle, a mean score 2.5±0.5 was observed corresponding to moderate to severe fibrosis according to the Metavir score (see FIG. 3A). For fibrotic mice receiving JWH-133 or compound 34 (GED), a score of 2±0 and 2.1±0.2 was observed, respectively. A decrease in the degree of fibrosis from severe to moderate fibrosis was observed with similar efficacy for both JWH-133 and GED.

Figure 3B:
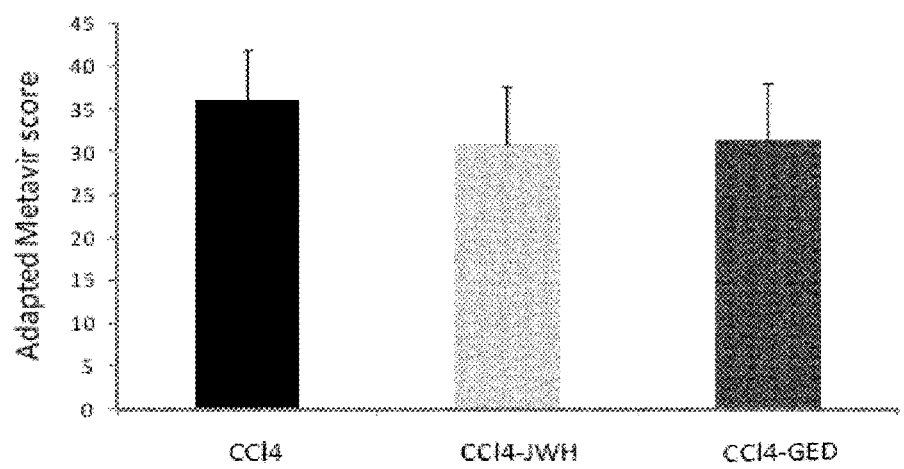

These results were confirmed using an adapted Metavir score (FIG. 3B): each liver section was analyzed blindly by 2 investigators for the quantification at low magnification (X5) of >30 portal tracts classified from F0 to F4 according to the METAVIR score (Score (of 1 section)=Σ(PTF1+PTF2+PTF3+PTF4)). Using this score it was demonstrated that JWH and GED decrease respectively by 14.2% and 12.5% the fibrotic score compared to untreated animals and that the therapeutic effect of the 2 tested molecules seems similar.

Example 3: Gene Expression Analysis of Liver Fibrosis Study

The effect of administration of compound 34 (GED) and the specific CB2 agonist (JWH-133) was evaluated on the level of gene expression of cytokines (IL-1, TNF-α) and genes involved in the mechanism of fibrosis by quantitative Real Time PCR.

Total RNA was isolated from livers using Rneasy kit (Macherey Nagel, Hoerdt, France) according to the manufacturer's instructions. RNA quantification was performed using spectrophotometry. After treatment at 37° C. for 30 min with 20-50 units of RNase-free DNase I (Roche Diagnostics Corporation, Indianapolis, Ind., USA), oligo-dT primers (Roche Diagnostics Corporation, Indianapolis, USA) were used to synthesize single-stranded cDNA. mRNAs were quantified using SYBR green Master Mix (Applera, Courtaboeuf, France) with murine specific oligonucleotides (see Table 2) in a GeneAmp Abiprism 7000 (Applera, Courtaboeuf, France). In each assay, calibrated and no-template controls were included. Each sample was run in triplicate. SYBR green dye intensity was analyzed using the Abiprism 7000 SDS software (Applera, Courtaboeuf, France). All results were normalized to the unaffected housekeeping gene β-actin.

TABLE 2

| Murine Genes | Primer Sequences (5' → 3') |
|---|---|
| β-actin | F: 5'-gggTCAgAAggATTCCTATg-3' (SEQ ID NO: 1)<br>R: 5'-ggTCTCAAACATgATCTggg-3' (SEQ ID NO: 2) |
| TNF-α | F: 5'-TgggAgTAgACAAggTACAACCC-3' (SEQ ID NO: 3)<br>R: 5' CATCTTTCTCAAAATTCgAgTgACAA-3' (SEQ ID NO: 4) |
| IL-1β | F: 5'-gATCCACACTCTCCAgCTgCA-3' (SEQ ID NO: 5)<br>R: 5'-CAACCAACAAgTgATATTCTCCATg-3' (SEQ ID NO: 6) |
| Collagen-1 | F: 5'-GAG TAC TGG ATC GAC CCT AAC CAA-3' (SEQ ID NO: 7)<br>R: 5'-ACA CAG GTC TGA CCT GTC TCC AT-3' (SEQ ID NO: 8) |
| α-SMA | F: 5'-CCT GAC GGG CAG GTG ATC-3' (SEQ ID NO: 9)<br>R: 5'-ATG AAA GAT GGC TGG AAG AGA GTC T-3' (SEQ ID NO: 10) |

Figure 4:
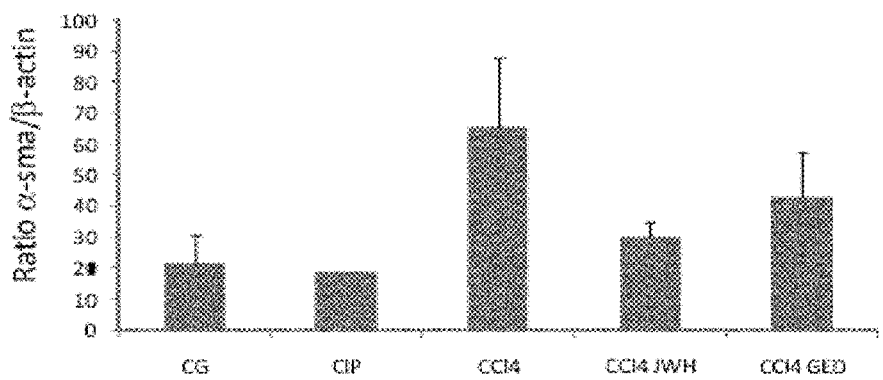
FIG. 4 depicts the effect of $CCl_4$, JWH-133+$CCl_4$ and compound 34+$CCl_4$ on α-SMA and collagen-1.
Figure 4:
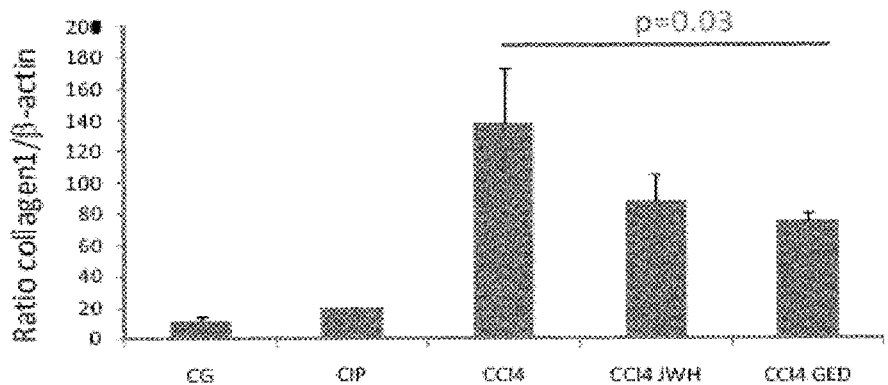

There was no significant modification of cytokine gene expression in the different groups of mice. With regards to the genes involved in the mechanism of fibrosis, there was an observed increase of expression of α-SMA and collagen-1 in animals with fibrosis ($CCl_4$ group) compared to control animals (CG and CIP groups). As seen in FIG. 4 and Table 3, there was a decrease in the level of α-SMA and collagen-1 in the GED and JWH-133 groups of mice as compared to the $CCl_4$ group (fibrosis control). For the level of collagen-1, the decrease was significant for the group of mice treated by compound 34 compared to the $CCl_4$ mice with respectively, 42.81±14.81, p=0.03 vs. 75.15±5.23. This biological data along with the histological improvement observed in mice treated with compound 34 suggests that compound 34 may have therapeutic anti-fibrotic properties.

TABLE 3

| Group | Collagen-1 | α-SMA |
|---|---|---|
| $CCl_4$ | 138.12 ± 34.68 | 65.51 ± 22.24 |
| JWH-133 + $CCl_4$ | 87.59 ± 16.97 | 30.07 ± 4.7 |
| Compound 34 + $CCl_4$ | 75.15 ± 5.23, p = 0.03 | 42.81 ± 14.81 |

Example 4: Liver Blood Enzyme Analysis of Liver Fibrosis Study

The effect of oral administration of compound 34 (GED) and the specific CB2 agonist (JWH-133) was evaluated on different liver biochemical parameters in the serum of mice: hepatic enzymes (alanine aminotransferase (AST) and aspartate aminotransferase (ALT)), Gamma GT and the Alkaline phosphatase.

As expected, 4 days after the last administration of $CCl_4$, no enhancement of AST, ALT and Alk P was observed in any groups of mice. Compound 34 was not associated with any enhancement of blood liver enzymes suggesting an absence of liver toxicity.

As evaluated by histology and liver markers, JWH-133 and compound 34 have similar anti-fibrotic effects in mice with liver fibrosis induced by repeated injections of $CCl_4$. As expected, JWH decreases hepatic fibrotic lesions by 14% and normalizes the liver concentration of collagen-1 mRNA. Compound 34 has a similar effect without liver toxicity. The data suggests that compound 34 may be the first compound with both anti-inflammatory and anti-fibrotic properties.

Example 5: Intestinal Fibrosis Study

This example describes an experiment to evaluate the effect of compound 34 on intestinal fibrosis. Chronic colitis was induced in C57bl6 mice by 3 cycles of 2.5% DSS (40,000-50,000 MW, TdB consultancy AB, Sweden) dissolved in sterile drinking water for 5 days followed by 7 days of regular drinking water.

The study consisted of 3 test groups (see Table 4): control group, DSS control group, GED (compound 34) group.

TABLE 4

| Test Group | Treatment | Dose Schedule |
|---|---|---|
| control<br>(10 mice) | $H_2O$ | Daily for 36 days |
| DSS control<br>(25 mice) | 2.5% DSS in<br>drinking $H_2O$ | 5 days on, 7 days<br>off for 36 days |
| compound 34<br>(25 mice) | 30 mM solution of<br>compound 34 in 0.5%<br>CMC administered via<br>oral gavage (200 uL)<br>and 2.5% DSS in<br>drinking $H_2O$ | cmpd. 34: daily<br>from day 13-36<br>DSS: 5 days on,<br>7 days off<br>for 36 days |

Figure 5:
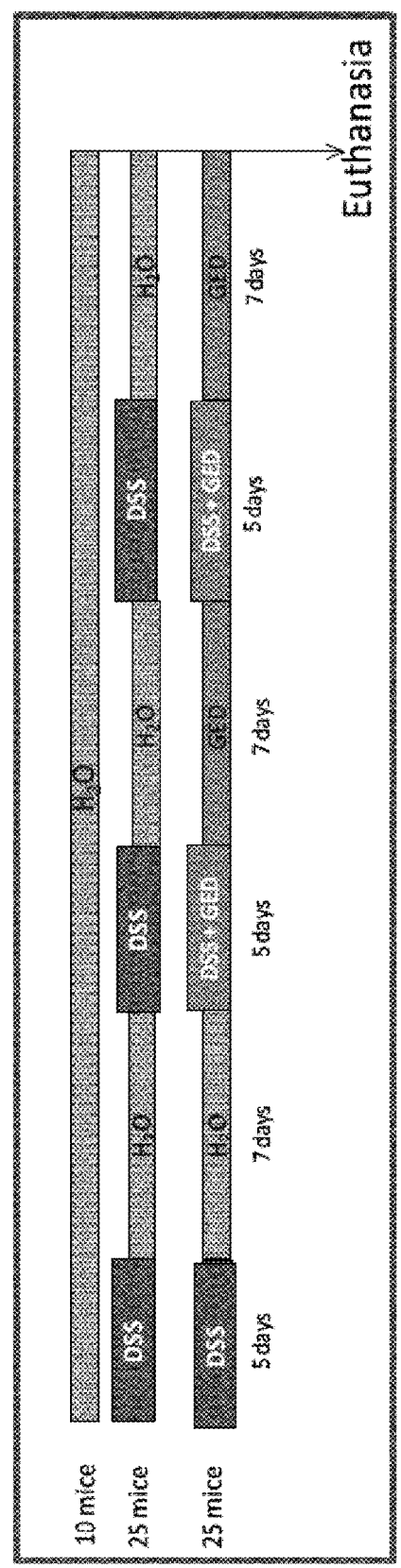
FIG. 5 depicts the intestinal fibrosis study schedule.

Compound 34 was used at its optimal dosage (30 mM) and administered by oral gavage daily after the second cycle of DSS and until euthanasia. Mice receiving DSS were checked twice a week for development of colitis by monitoring body weight. Euthanasia of mice was performed one week after the third cycle of DSS (see FIG. 5). Evaluation of the size and weight of the colon was evaluated post mortem.

Example 6: Analysis of Intestinal Fibrosis Study

A. Colon Ratio Weight/Size

Figure 6A:
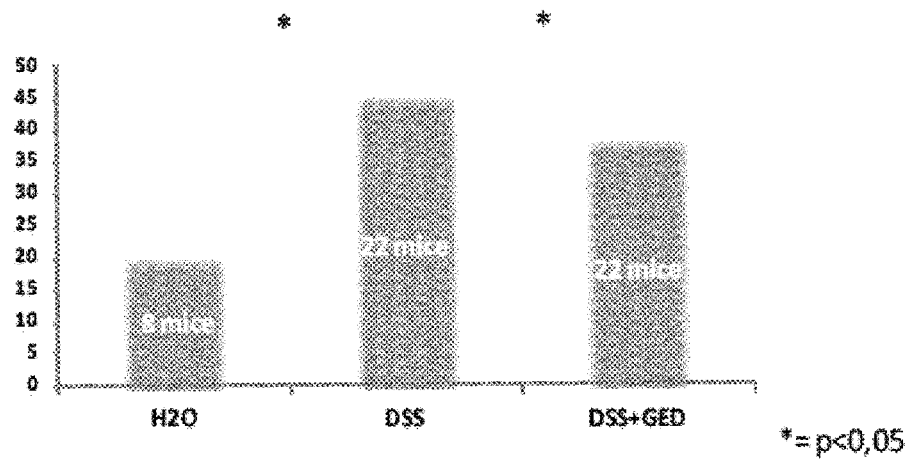
FIGS. 6A and 6B depict the effect of compound 34 on the colons of mice having intestinal fibrosis.
Figure 6B:
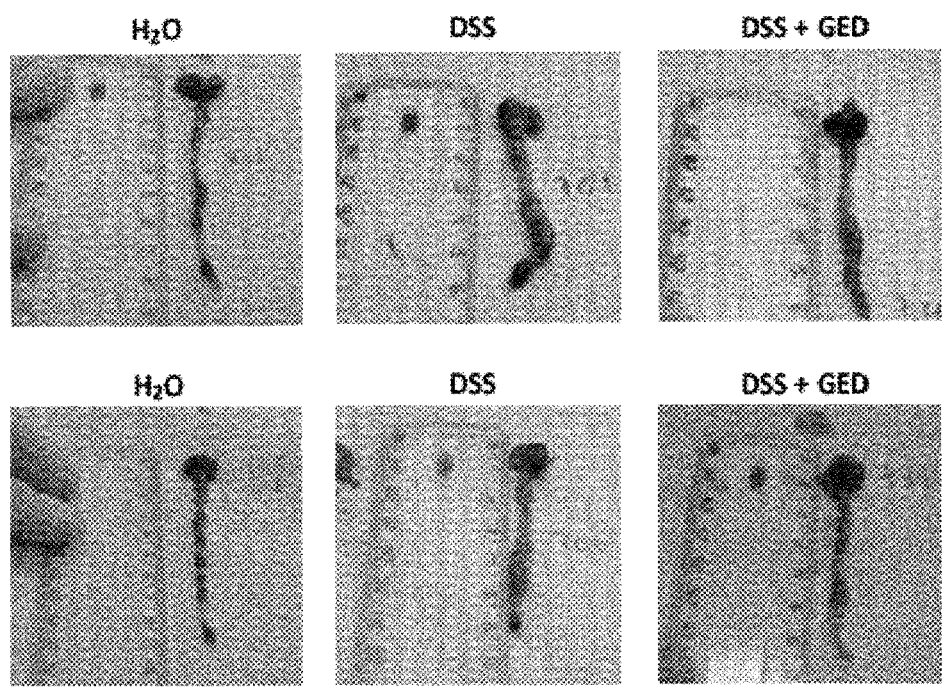

Intestinal fibrosis is characterized by a shortening and thickening of the colon and adherences. The measure of the ratio weight/size of the colon is an indicator of the level of inflammation and fibrosis. As seen in FIG. 6A, a significant increase of 124% in the ratio of colon weight/size was observed in the DSS mice receiving the vehicle compared to control mice receiving only regular water, with respectively 44.98±6.31 vs 20.11±3.91, p<0.05. These results are illustrated by an important shortening of the colon in DSS mice (FIG. 6B). Compound 34 causes a 34% reduction in the profibrotic effect of DSS leading to a significant decrease ratio weight/size of the colon of 38.13±7.82 vs 44.98±6.31 (p<0.05) compared to DSS mice receiving the vehicle (FIG. 6A). Accordingly, it reduces the morphological signs of fibrosis such as the shortening and the thickening of the colon and it decreases the collagen deposit in the colon (FIG. 6B).

B. Inflammation Level Estimated by Histology

Rings of the transverse part of the colon were sampled (post mortem) and fixed in 4% formaldehyde and embedded in paraffin for histological analysis. Sections (4 µm) were stained with May-Grunwald-Giemsa and a multiparametric histological scoring (0 to 18) was performed blindly by two investigators. This staining allowed the quantification of inflammation. Histological grades, reflecting the inflammation level, were assigned based on the intensity of cellular infiltrate in the mucosa, its extension in sub-mucosa layers and the presence of epithelial lesions (see Table 5).

TABLE 5

| Segment | Grade | Description |
|---|---|---|
| Severity | 0 | None |
| | 1 | Slight |
| | 22 | Moderate |
| | 3 | Severe |
| Extent | 0 | None |
| | 1 | Mucosa |
| | 2 | Mucosa and submucosa |
| | 3 | Transmural |
| Regeneration | 4 | No Tissue Repair |
| | 3 | Surface epithelium not intact |
| | 2 | Regeneration with crypt depletion |
| | 1 | Almost complete regeneration |
| | 0 | Complete regeneration or normal tissue |
| Crypt damage | 0 | None |
| | 1 | Basal ⅓ damaged |
| | 2 | Basal ⅔ damaged |
| | 3 | Only surface epithelium intact |
| | 4 | Entire crypt and epithelium lost |
| Percentage involvement | 1 | 1-25% |
| | 2 | 26-50% |
| | 3 | 51-75% |
| | 4 | 76-100% |

Figure 7:
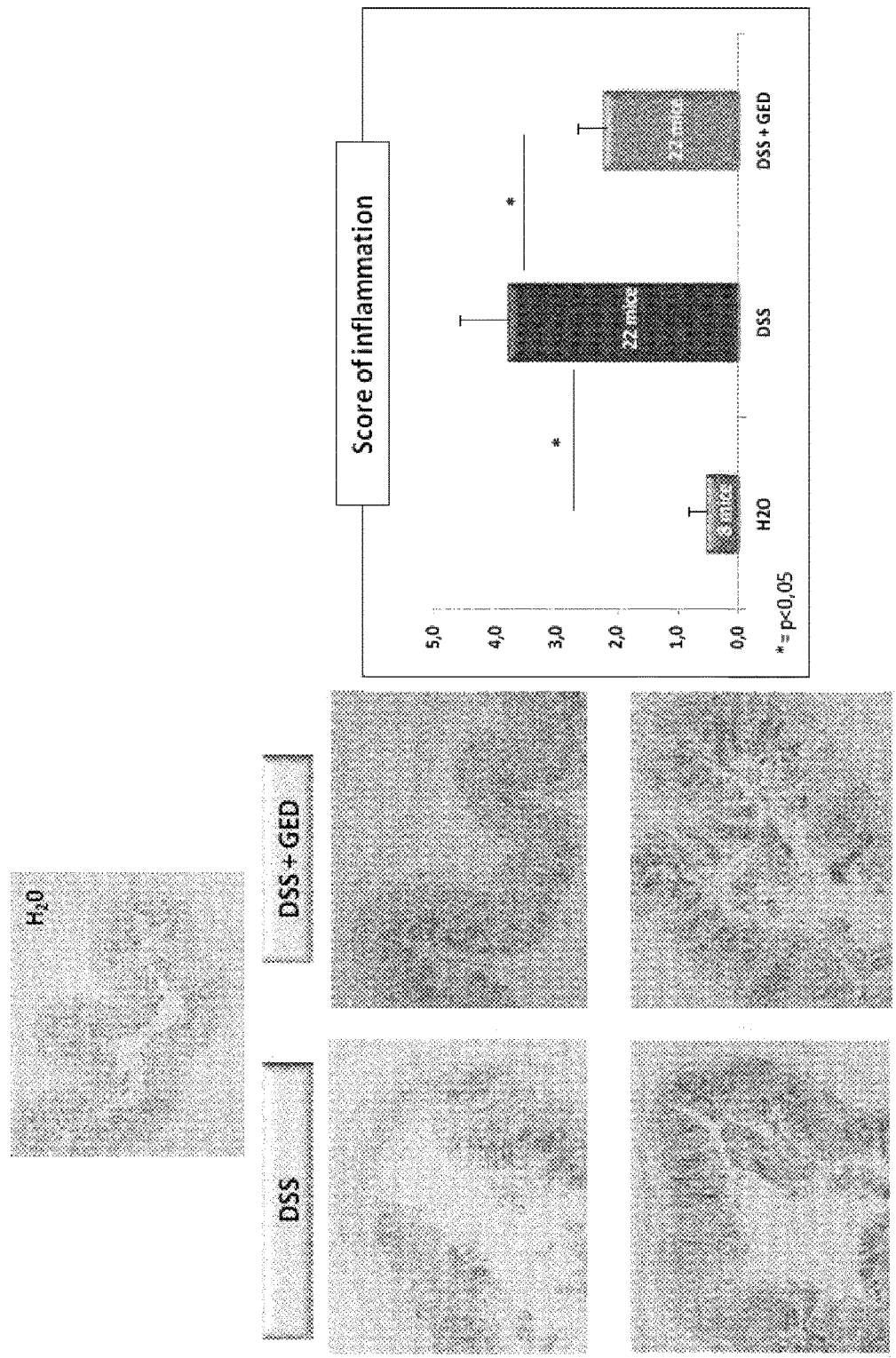
FIG. 7 depicts the anti-inflammatory effect of compound 34 on the colons of mice having intestinal fibrosis.

The inflammatory status was evaluated at the histological level for each colon of mice using a classical MGG staining. As expected, significant and strong inflammation was observed in the group of mice receiving the DSS compared to control mice receiving regular water, with respectively 3.77±0.80 vs. 0.50±0.33, $p<0.05$ (see FIG. 7). This result confirms the induction of inflammation by the 3 cycles of DSS. A significant decrease in the inflammation level was observed in DSS mice receiving compound 34 as compared to DSS mice receiving only the vehicle with respectively, 2.18±0.48 vs. 3.77±0.80, $p<0.05$.

C. Level of Fibrosis

C1. Evaluation by Picrosirius Red Staining

Samples of colon obtained were promptly fixed with 10% buffered formalin in PBS (pH 7.4) for 3 h, dehydrated in graded ethanol and embedded in low-temperature-fusion paraffin. Formalin-fixed colonic tissue was processed and 5 µm thick paraffin sections were stained with Picrosirius red staining for histological analysis. Pictures were obtained with a ×20 objective. Each section was analyzed blindly by 3 different experimenters for the quantification of the degree of fibrosis using a score from 0 to 4.

Figure 8:
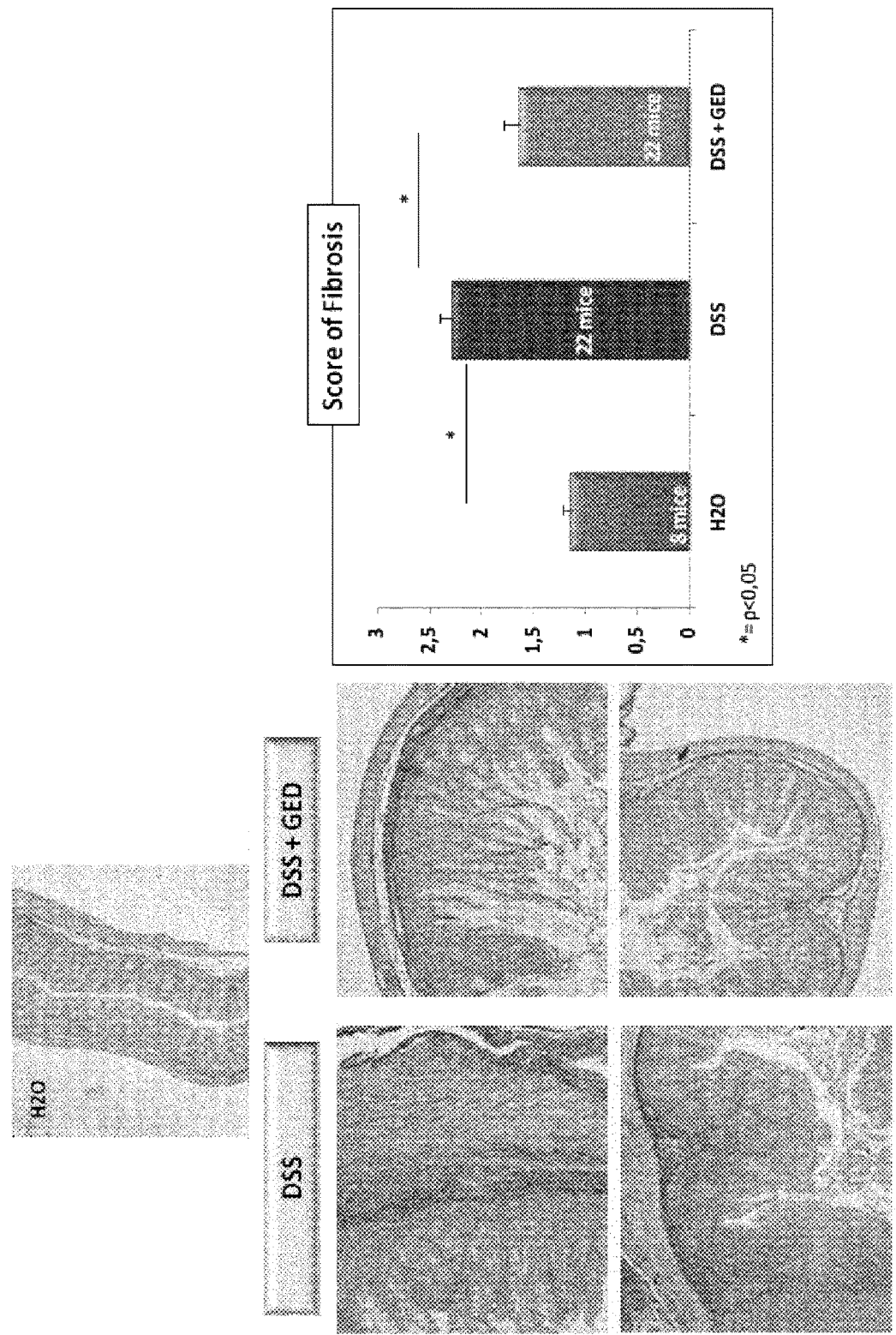
FIG. 8 depicts the effect of compound 34 on the colons of mice having intestinal fibrosis.

A significant increase of the level of fibrosis was observed in the colon of DSS mice compared to control mice with respectively 2.27±0.12 vs 1.12±0.07 (see FIG. 8). This result confirms that chronic inflammation induced by 3 cycles of DSS induces intestinal fibrosis. It also confirms that administration of compound 34 to DSS mice decreases the level of fibrosis compared to DSS mice receiving only the vehicle (1.625±0.15 vs. 2.27±0.12, $p<0.05$).

C2. Evaluation by Trichrome Masson's staining

A trichrome masson's and collagen staining were used in this evaluation of the level of colonic fibrosis. Samples of colon obtained were promptly fixed with 10% buffered formalin in PBS (pH 7.4) for 3 h, dehydrated in graded ethanol and embedded in low-temperature-fusion paraffin. Serial 3 µm sections were incubated for 40 min in methanol and 3% hydrogen peroxide solution and then rinsed in PBS. Intestinal fibrosis was scored as absent, mild, or severe, depending on the density and extent of trichrome-positive connective tissue staining and disruption of tissue architecture.

C3. Evaluation of Collagen Levels

For the immunohistochemical analysis, tissue specimens from the colon were fixed in fresh 4% paraformaldehyde (PFA)/PBS solution for 3 h at room temperature, dehydrated in a graded ethanol series, and embedded in low-temperature-fusion paraffin. 3-µm-thick sections were incubated in methanol for 40 min and then in 3% hydrogen peroxide for 5 min. Samples were incubated overnight with specific antibodies against collagen types I-III (Abcam), connective tissue growth factor (CTGF) (Abcam), Platelet Derived Growth factor (PDGF), SMAD2/3, the main markers of fibrosis. The samples were washed for 5 min with PBS and incubated with streptavidin-biotin-peroxidase conjugated secondary antibody (Dako LSAB Corporation, cod K0675, Dako-Cytomation, Milano). After a wash in PBS for 10 min the sections were subjected to incubation with 3,3-diaminobenzidine-tetrahydrochloride for 1-3 min.

The specificity of immune reaction was performed omitting the primary antibodies Finally the samples were stained with hematoxylin of Mayer and observed under the Olympus BX51 Light Microscope (Olympus, Optical Co. Ltd., Tokyo, Japan).

Figure 9A:
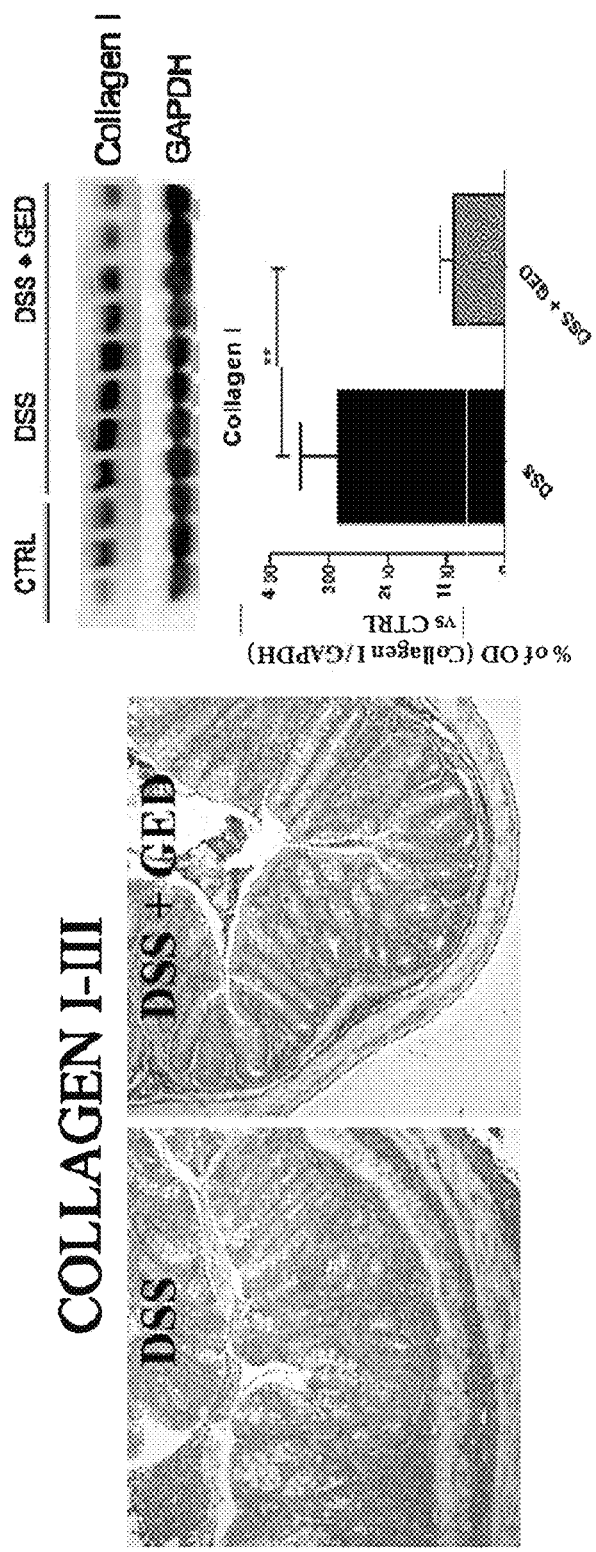
FIGS. 9A, 9B, 9C, 9D, and 9E depict the effect of compound 34 on the colons of mice having intestinal fibrosis using an immunohistochemical analysis of the main markers of fibrosis (Collagen I-III, CTGF, SMAD 2/3, PDGF, α-SMA, and TGF-β1).
Figure 9B:
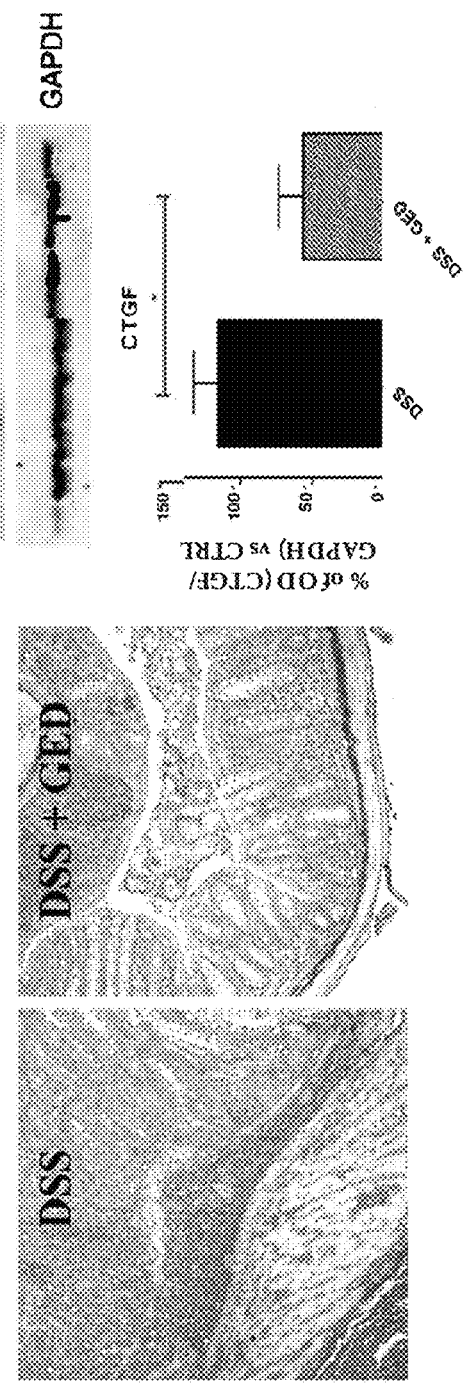
Figure 9C:
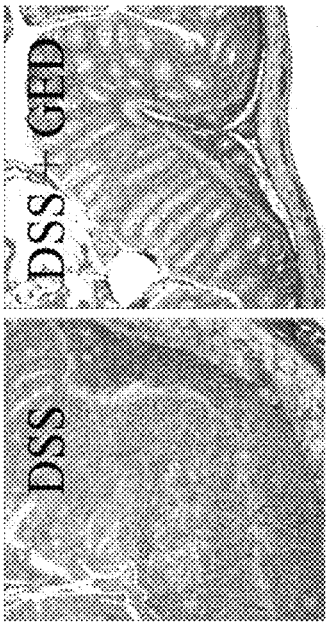
Figure 9C:
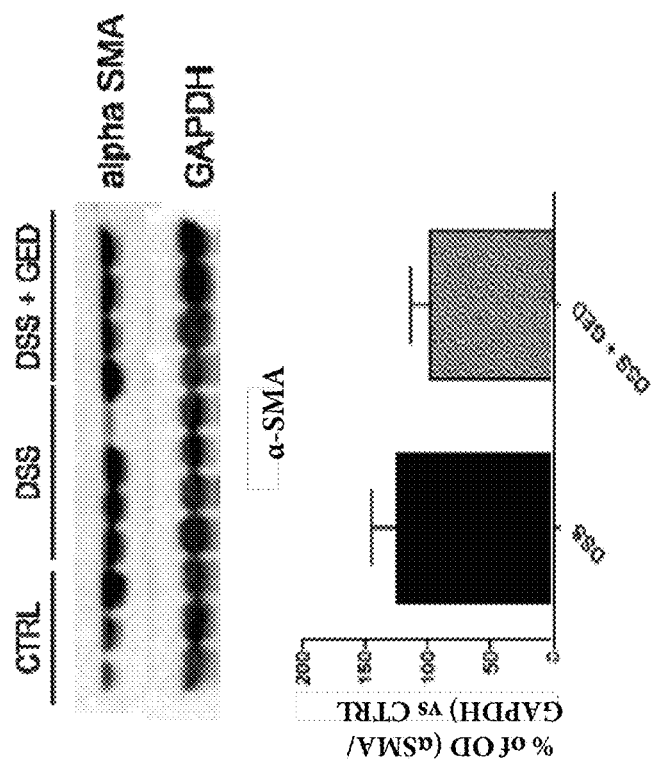
Figure 9D:
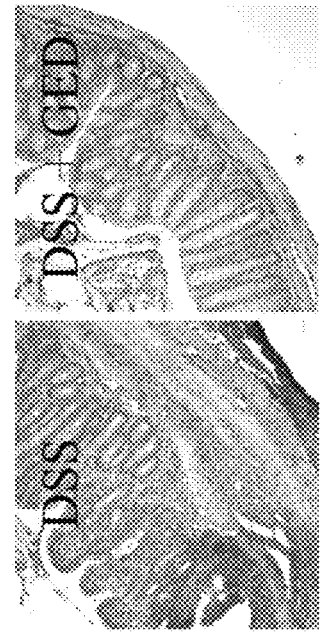
Figure 9D:
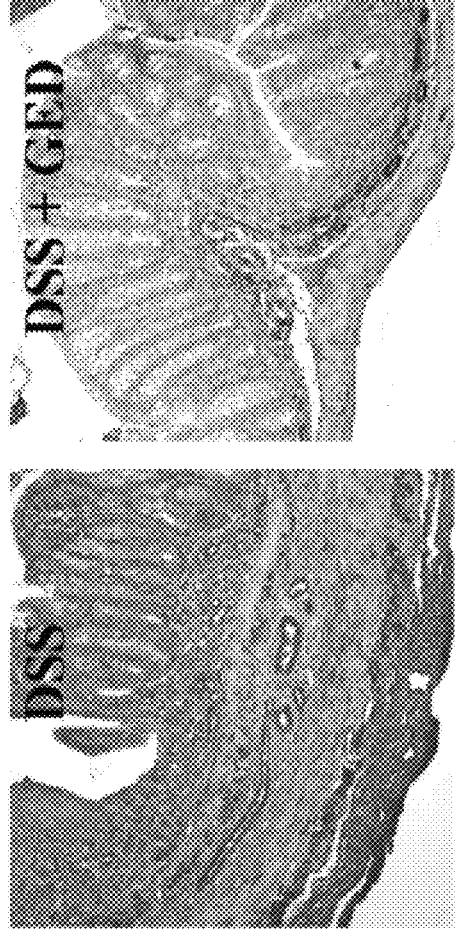
Figure 9E:
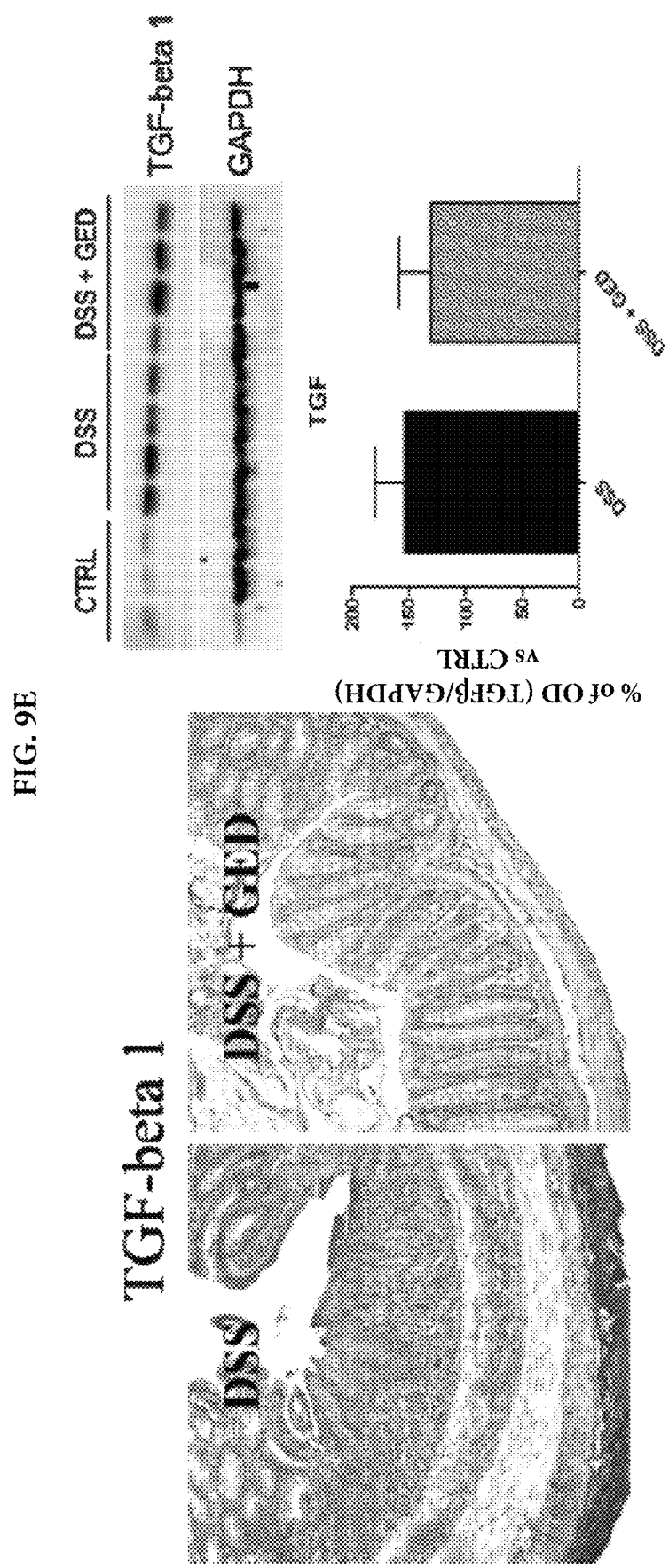

In the immunohistochemical analysis (×20) of collagens I-VII in colon from DSS and control mice, the staining of collagens I-VII in large intestine of DSS mice was localized mainly within connective tissue of submucosa and muscularis propria, where strong staining of collagen was observed (see FIG. 9A). As shown in FIG. 9A, administration of compound 34 is associated with a decrease in the collagen staining indicating that it has improved the fibrosis and reduces the development of intestinal fibrosis.

In addition to anti-inflammatory effects, administration of compound 34 decreases rapidly molecular events leading to fibrosis and prevents the intestinal fibrotic lesions induced by DSS in mice.

For the Western blot analysis, 0.5 cm of frozen colonic samples were homogenized in RIPA Buffer containing 50 mM Tris HCl pH 7.6, 150 mM NaCl, 1.5 mM $MgCl_2$, 5 mM EDTA, 1% Triton-X and 10% Glycerol, supplemented with 100 mM Sodium Fluoride (NaF), 2 mM Sodium Orthovanadate ($Na_3VO_4$), 10 mM Sodium Pyrophosphate (NaPPi), 1 mM phenylmethanesulphone (PMSF) and a classical protease-inhibitor cocktail containing 10 µg/mL Leupeptin and Aprotinin.

For each sample, 30 µg of protein was separated by PAGE and electroblotted. Nitrocellulose membranes (100% pure) were incubated (according with a specific protocol for each antibody) with primary antibodies directed against CTGF, Collagen-I and GAPDH (purchased from Abcam, Cambridge, UK; 1:1000 for 2 h at RT), diluted in 5% non-fat milk in 0.1% TBS-t. Membranes were subsequently washed in TBS-t 0.1% and incubated with secondary horseradish peroxidase-conjugated antibodies (anti-Rabbit and anti-Mouse; Sigma Aldrich; 1:20000 for 1 h at RT) diluted in 5% non-fat milk in 0.1% TBS-t. Finally, immunodetection was performed with SuperSignal West Pico chemiluminescent substrate (Thermo Scientific Pierce, Erembodegem) according to manufacturer's protocol. Membranes were exposed to autoradiography film (Fuji Photo Film Co., Dusseldorf, Germany). Optical density of target bands was determined using a computer-assisted densitometer and the ImageJ public domain software (W. S., Rasband, ImageJ, U. S. National Institutes of Health, Bethesda, Md.; http://rsb.info.nih.gov/ij/, 1997-2011). Tissue levels were expressed as units of Optical Density (OD) per quantity of total proteins, normalized with internal control GAPDH and the results were expressed as percentage of control groups.

Using the IHC methods and specific antibodies, a reduction of the main markers of fibrosis (Collagen I-III, CTGF, SMAD 2/3, PDGF, α-SMA, and TGF-β1) was observed in the colon of DSS mice having received the GED compared to colitic mice receiving the vehicle (see FIG. 9A-9E).

Figure 10:
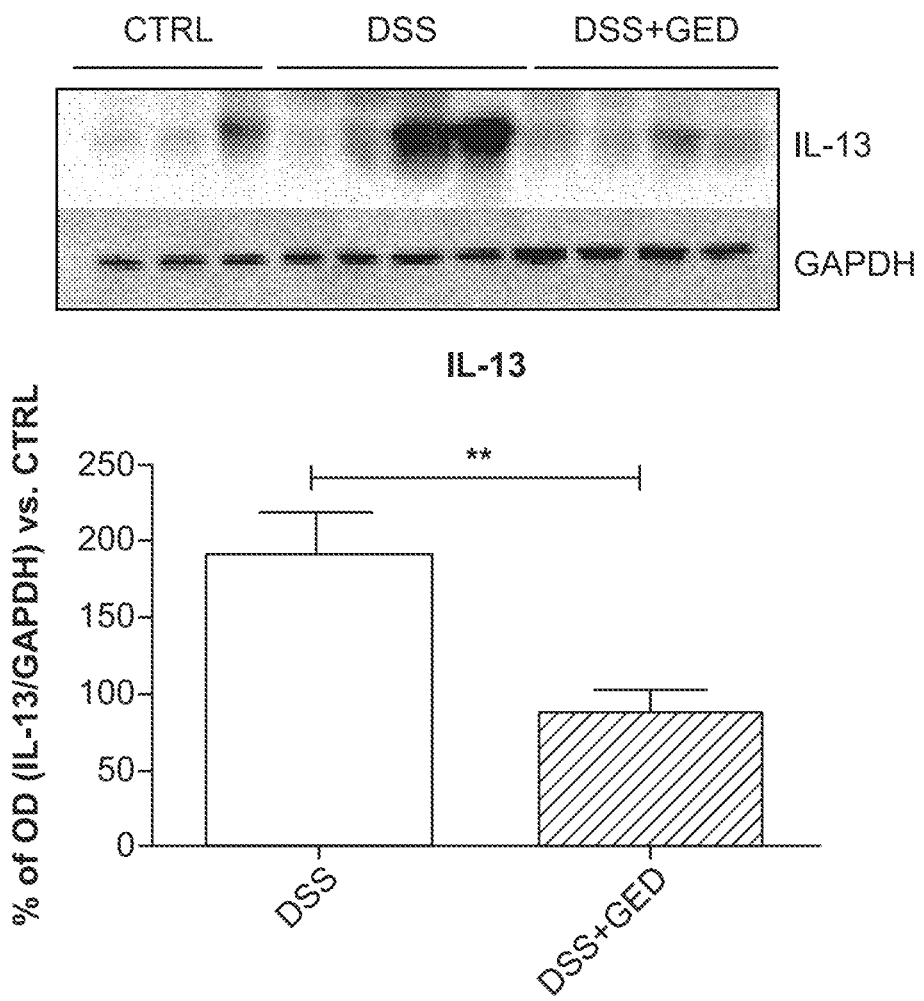
FIG. 10 depicts the effect of compound 34 on the colons of mice having intestinal fibrosis using a Western Blot analysis.

These results were confirmed using Western blot method and the quantification of different fibrosis markers was performed on the whole colon samples (see FIG. 10). As seen in Table 6, a significant decrease of the expression of collagen I, CTGF and IL-13 was observed in the colitic mice treated by GED compared to colitic mice receiving only the vehicle (Collagen I 90.75±19.91 vs. 284.4±63.86, p=0.012, for CTG 55.75±17.53 vs. 115.1±16.88, p=0.029 and IL-13 88.88±14.01 vs. 189.5±28.71, p=0.007).

TABLE 6

|  | DSS | DSS + GED | p |
| --- | --- | --- | --- |
| α-SMA | 125.4 ± 19.45 | 97.88 ± 15.66 | 0.282 |
| Collagen I | 284.4 ± 63.86 | 90.75 ± 19.91 | 0.012 |
| CTGF | 115.1 ± 16.88 | 55.75 ± 17.53 | 0.029 |
| IL-13 | 189.5 ± 28.71 | 88.88 ± 14.01 | 0.007 |
| TGF-β1 | 153.6 ± 26.25 | 130.5 ± 28.02 | 0.5 |

Example 7: Intestinal Fibrosis Study

This example describes an experiment to evaluate the effect of compound 34 (GED) in treating intestinal fibrosis.
Materials and Methods
In Vitro Experiments A total of 60 wild type C57BL/6 mice, purchased from Janvier (Le Genest-St-Isle, France) were included in the study. All mice were maintained in a specific pathogen-free facility of the Pasteur Institute in Lille (France). Animal experiments were performed according to the governmental guidelines N°68/609/CEE.
Induction of Chronic Colitis Chronic colitis and fibrosis were induced in mice by oral administration of 2.5% (w/v) DSS in drinking water, for three cycles (5 day DSS, 7 days of water). Animals were monitored daily for food and fluid intake and were weighed at the beginning of the study and thereafter regularly every three days.
Experimental Design The mice were randomly divided into two groups: i. DSS and ii. DSS+GED. Each group consisted of 25 mice and was compared with 10 control animals, which received only water. GED (30 mg/kg/mouse) was dissolved in a solution containing 0.5% Carboxymethylcellulose sodium salt (CMC; MW: 90,000 Da; Sigma Aldrich) and 1% Tween 80 and was administered daily by oral gavage (100 µl/mouse). GED was administered at the beginning of second cycle.
Assessment of Colitis Course Animals were observed daily for fluid intake, weight changes, and examined for signs of colitis including weight loss, diarrhoea, rectal bleeding and prolapse as well as signs of systemic inflammation such as piloerection, lethargy, and periorbital exudates.
Samples Recovery and Preparation Finally, seven days after the last DSS cycle administration, the animals of each group were sacrificed by cervical dislocation under deep $CO_2$ anaesthesia and undergone to laparotomy. The colon were visualized and rapidly excised. The length of the whole colon-rectum and the weight of the distal 8 cm of colon-rectum were measured.
Assessment of Macroscopic and Microscopic Colonic Lesions The macroscopic colonic lesions including dilation, thickness and stenosis were scored by an independent observer, unaware of the mice treatment. Tissue specimens from the colon were dissected and immediately frozen or fixed in fresh 4% formaldehyde (FA)/PBS solution for 3 h at room temperature followed by the standard procedure for paraffin embedding. Paraffin embedded tissues transversally sectioned at 3 µm were subject to Hematoxylin/Eosin staining, to assess the inflammatory degree, and Masson trichrome to better assess connective tissue and fibrosis. The stained sections were then blindly observed under an Olympus BX51 Light Microscope (Olympus, Optical Co. Ltd., Tokyo, Japan) by two pathologists which have performed the histological score evaluating: i. presence of ulcers (0=absent, 1=little ulcers, 2=big ulcers); ii. the inflammatory degree (0=absent 1=mild, 2=moderate and 3=severe); iii. depth of lesions (0=absent, 1=lesions extending in the submucosa, 2=lesions in the muscolarispropria and 3=lesions in the serosa); iv. degree of fibrosis (0=absent 1=mild, 2=moderate and 3=severe). The degree of intestinal inflammation was assessed according to the density and extent of chronic inflammatory infiltrate, loss of goblet cells, and bowel wall thickening. A total microscopic score will be obtained as sum of all scores (maximum score possible=10).

Intestinal fibrosis was scored as absent, mild, or severe, depending on the density and extent of trichrome-positive connective tissue staining and disruption of tissue architecture.
Immunohistochemistry Tissue specimens from the colon, dissected and fixed in fresh 4% formaldehyde (FA)/PBS solution for 3 hours at room temperature, were dehydrated in a graded ethanol series, and embedded in low-temperature-fusion paraffin. 3-m-thick sections were incubated in a solution of methanol and 3% hydrogen peroxide for 45 min.

Samples were incubated overnight with specific antibodies against α-smooth muscle actin (α-SMA, Abcam), collagen types I-III (Abcam), TGF-β1 (Abcam), connective tissue growth factor (CTGF) (Abcam), pSmad3 and Smad3 (Cell Signaling), Smad7 (Imgenex) PPART (Cell Signaling). The samples were washed 5 min with PBS and incubated with streptavidin-biotin-peroxidase conjugated secondary antibody (Dako LSAB Corporation, cod K0675, DakoCytomation, Milano). After one wash in PBS for 10 min the sections are subject to incubation with 3,3-diaminobenzidine-tetrahydrochloride for 1-3 min. The counterstaining of nuclei was obtained by Hematoxilin Eosin. The specificity of immune reaction was effected keeping off the primary antibodies. Finally the samples were stained with hematoxylin of Mayer and observed under the Olympus BX51 Light Microscope (Olympus, Optical Co. Ltd., Tokyo, Japan).
Western Blot Analysis 0.5 cm of frozen colonic samples were cut and mechanically homogenized in RIPA Buffer containing 50 mMTrisHCl pH 7.6, 150 mMNaCl, 1.5 mM $MgCl_2$, 5 mM EDTA, 1% Triton-X and 10% Glycerol, supplemented with 100 mM Sodium Fluoride (NaF), 2 mM Sodium Orthovanadate (Na3VO4), 10 mM Sodium Pyrophosphate (NaPPi), 1 mMphenylmethanesulphone (PMSF) and a classical protease-inhibitor cocktail containing 10 μg/mL Leupeptin and Aprotinin.

30 μg of protein for each sample were separated by PAGE and electroblotted. 100% pure Nitrocellulose membranes were incubated (according with a specific protocol for each antibody) with primary antibodies directed against TGF-β1, CTGF, α-SMA, Collagen-I and GAPDH (purchesed from Abcam, Cambridge, UK; 1:1000 for 2 h at RT), and IL-13 (purchased from Antibodies online; 1:1000 for 2 h at RT) diluited in 5% non fat-milk in 0.1% TBS-t. Membranes were subsequently washed in TBS-t 0.1% and incubated with secondary horseradish peroxidase-conjugated antibodies (anti-Rabbit and anti-Mouse; Sigma Aldrich; 1:20000 for 1 h at RT) diluted in 5% non fat-milk in 0.1% TBS-t. Finally, immunodetection was performed with SuperSignal West Pico chemoluminescent substrate (Thermo Scientific Pierce, Erembodegem) according to manufacturer's protocol. Membranes were exposed to autoradiography film (Fuji Photo Film Co., Dusseldorf, Germany). Optical density of target bands was determined using a computer-assisted densitometer and the ImageJ public domain software (W. S., Rasband, ImageJ, U. S. National Institutes of Health, Bethesda, Md.; http://rsb.info.nih.gov/ij/, 1997-2011). Tissue levels were expressed as units of Optical Density (OD) per quantity of total proteins, normalizing with internal control GAPDH and the results were expressed as percentage of control groups.

In Vivo Experiments

Cell Cultures

Human colon cancer cell line HT-29 (ATCC HTB-38) and colonic intestinal fibroblasts (ATCC human CDD-18 co) were grown in Dulbecco's modified Eagle's medium (DMEM) and Alpha-Modified Eagle's medium, respectively, 100 U/ml penicillin and 100 μg/ml streptomycin supplemented with 10% fetal bovine serum (FBS). Cell cultures were maintained in a humidified atmosphere of 95% air and 5% $CO_2$ at 37° C.

PPARγ Knock Down Cells Generation

PPARΤ knock down HT29 were obtained using the pSUPER.retro system (OligoEngine). Forward and reverse target sequences corresponding to nucleotides 105-123 of the human PPARγ mRNA (5'-GCCCTTCACTACTGTTGAC-3' (SEQ ID NO: 11)) were cloned into the BglII/XhoI restriction sites of the pSUPERretro vector (pRS) giving the ShPPAR construct. A negative control pRS plasmid containing the sequence 5'-ACGCTGAGTACTTCGAAAT-3' (SEQ ID NO: 12) targeted against the luciferase gene was also generated (ShLuc construct). Both constructions were transfected in HT-29 and Caco-2 cells using Nucleofector technology from AmaxaBiosystems, according to the manufacturer's protocol. Stably transfected clones were selected 24 h post-transfection with complete culture medium supplemented with puromycin (5 μg/ml). The silencing of PPARg expression was checked by quantitative RT-PCR and western-blot analysis. Once established, ShPPAR and ShLuc cell lines were maintained in complete medium supplemented with 2.5 μg/ml puromycin.

Experimental Design

Fibrotic phenotype was induced by stimulating hCCD-18 and HT29 with TGF-β 1 ng/mL and 10 ng/mL for 4 days, respectively, dissolved in serum-free medium. 1 mM for GED (195.22 g/mol) was administrated during the differentiation period. In addition, the potential dependence on PPART activation has been investigated by using GW9662, a specific antagonist of this receptor. 10-5 M GW9662 has been administrated 4 h before to start the TGFβ-induced differentiation.

Quantitative RT-PCR

Total RNA was extracted with a Nucleospin RNA kit (Macherey-Nagel, Hoerdt, France). After RNAse inactivation, the total RNA was cleaned of trace genomic DNA via a DNAse treatment and eluted in RNAse-free, DEPC-free water. The purity of the RNA was evaluated by UV spectroscopy on a Nanodrop system from 220 to 350 nm and profiling on an Agilent 2100 bioanalyzer. One μg of total RNA was used to perform a Quantitative RT-PCR by using LightCyclerFastStart DNA Master SYBR Green I from Roche Diagnostics (Indianapolis, Ind.) according to the manufacturer's protocol.

Results

In Vivo Experiments

Clinical and Macroscopic Findings on Chronic Colitis in Mice

Figure 11:
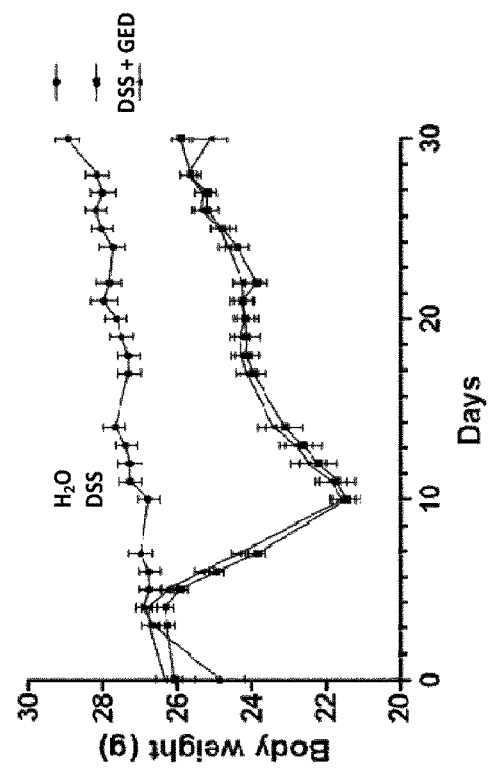
FIG. 11 shows a body weight curve in mice treated with DSS and DSS+GED.

Chronic oral administration of DSS induced loss of body weight in all chronic mice starting from the last day of first DSS cycle (day 5). At day 10 the mice receiving DSS showed a lower body weight compared to the control mice with respectively 23.88±0.31 vs. 25.27±0.35 $p<0.05$ (FIG. 11)

Moderate to severe diarrhea were observed in 70% of DSS treated mice and 50% of GED mice on the seventh day of DSS oral administration. In the same period systemic manifestations, such as piloerection, periorbital exudates and/or lethargy, were observed in 40% of DSS mice and 30% of GED mice. At no stage frank rectal bleeding or rectal prolapse were observed. The mice were sacrificed on day 15 and day 30, respectively, and the colon was subjected to macroscopic evaluation by measuring of colon weight (referred to the last 8 cm of the distal large bowel) and colon length and by observing the presence of adhesions, strictures, dilatation, thickness that was scored as 0 if absent; 1 if mild or moderate; and 2 if severe. The total macroscopic score was calculated as sum of all these score.

The effects of GED administration on course and macroscopic findings of DSS-induced chronic colitis in mice are summarized in Table 7, indicating that GED ameliorates macroscopic lesions in and chronic DSS-induced colitis and reduce the morphological signs of fibrosis.

All the macroscopic features observed in DSS treatments showed, in both models, significant variation that indicated an effective ability of DSS to induce a severe tissue damage. All macroscopic lesions were ameliorated by the GED treatment determining significant differences between DSS and DSS plus GED total macroscopic scores. Colon weight and colon weight/body weight ratio showed no significant variation following the GED treatment, while colon length appeared significantly restored. Direct observation of colons showed, indeed, an evident shortening and dilatation in majority of DSS-treated samples and a remission of these features on GED treated mice.

TABLE 7

Effect of GED Administration on Course and Macroscopic Findings of Chronic colitis

| Parameters | CHRONIC | | |
|---|---|---|---|
| | H₂O | DSS | DSS + GED |
| Duration of DSS treatment | 30 days | 30 days | 15 days |
| Mortality (n. mice) | 0 | 2 | 0 |
| Body weight | 28.95 ± 0.331 | 25.93 ± 0.223** | 25.132 ± 0.458** |
| Colon weight | 0.171 ± 0.005 | 0.283 ± 0.006*** | 0.269 ± 0.007*** |
| Colon weight/body weight ratio | 0.29 ± 0.0051 | 0.26 ± 0.007** | 0.27 ± 0.012**/¥¥ |
| Colon length | 8.52 ± 0.093 | 6.304 ± 0.0.09** | 7.092 ± 0.16**/ |
| Dilation | np | 1.35 ± 0.165** | 1.12 ± 0.185**/¥¥ |
| Thickness | np | 1 ± 0.154** | 0.48 ± 0.108**/¥ |
| Stenosis | np | 0.364 ± 0.151** | 0.32 ± 0.114**/¥ |
| Adhesions | np | 0.348 ± 0.135** | 0.12 ± 0.1¥¥ |
| Total macroscopic score | np | 3.112 ± 0.31** | 2.02 ± 0.26**/¥¥ |

Data are expressed as mean ± SEM;
np = not present;
* = $p < 0.05$ vs H₂O;
** = $p < 0.01$ vs H₂O;
*** = $p < 0.005$ vs H₂O;
¥ = $p < 0.05$ vs DSS;
¥¥ = $p < 0.01$ vs DSS;
¥¥¥ = $p < 0.005$ vs DSS Thus, the ratio weight/size of the colon was used as further indicator of the level of inflammation and fibrosis. A significant increase of 124% in the ratio was observed in the DSS-receiving mice compared to control mice receiving only regular water, with respectively 44.98±6.31 vs. 20.11±3.91 (p<0.05). GED led to a significant decrease of ratio weight/size of the colon compared to DSS mice (38.13±7.82 vs. 44.98±6.31 (p<0.05)) causing a 26% reduction respect to the profibrotic effect of DSS. Accordingly, GED is able to reduce the morphological signs of fibrosis such as shortening and thickening of the colon.

Microscopic Findings on Chronic Colitis

Several histological parameters were scored on the bases of intensity of cellular infiltrate in the mucosa, inflammation extension in sub-mucosa layers and the presence of epithelial lesions and collagen deposition. A significant and strong inflammation was observed in the group of mice receiving the DSS compared to control mice receiving regular water. The histological features in both models showed mucosal ulceration and degeneration, decrease of goblet cells, wide inflammatory cellular infiltration, and submucosal edema. All these findings appeared more emphasized in DSS-induced chronic colitis and a wide thickening of the colon wall was evident. In addition, the chronic model showed an evident regeneration of crypts and a possible spontaneous recovering of inflammatory degree in the long-term treatments (FIG. 12).

The level of fibrosis was observed by Masson's trichrome staining, specific for collagen deposition. A significant increase of the level of fibrosis was observed not only in the colon of DSS mice compared to control mice but also between the two treatments (FIG. 12). This evidence, together with the observation of a lower inflammatory degree, seems consistent with the postulate that fibrosis begins from an inflammatory response but, subsequently, may progress independently from it.

Figure 12:
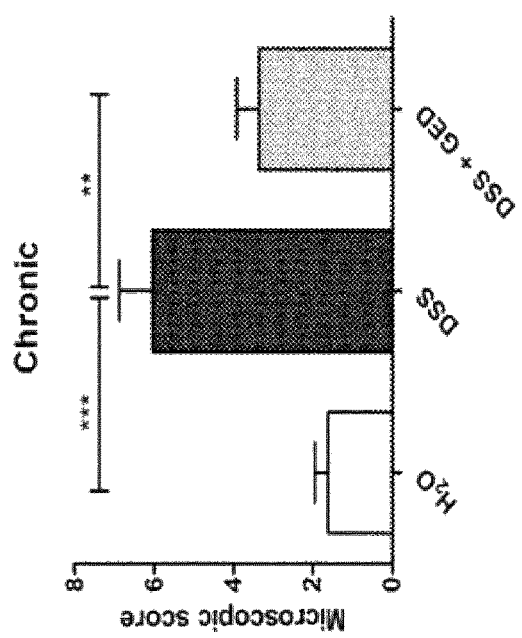
FIG. 12 shows the level of fibrosis in the colon of mice treated with DSS and DSS+GED compared to control mice receiving regular water.

Total microscopic scores were assigned and demonstrated that high inflammatory degree and levels of fibrosis, induced by 1 and 3 cycles of DSS, decreased significantly following the daily oral administration of GED (3.36±0.55 for GED vs. 6.45±0.82 for DSS, p<0.01) (FIG. 12).

Evaluation of Tissue Levels of Main Fibrosis Markers

Figure 13A:
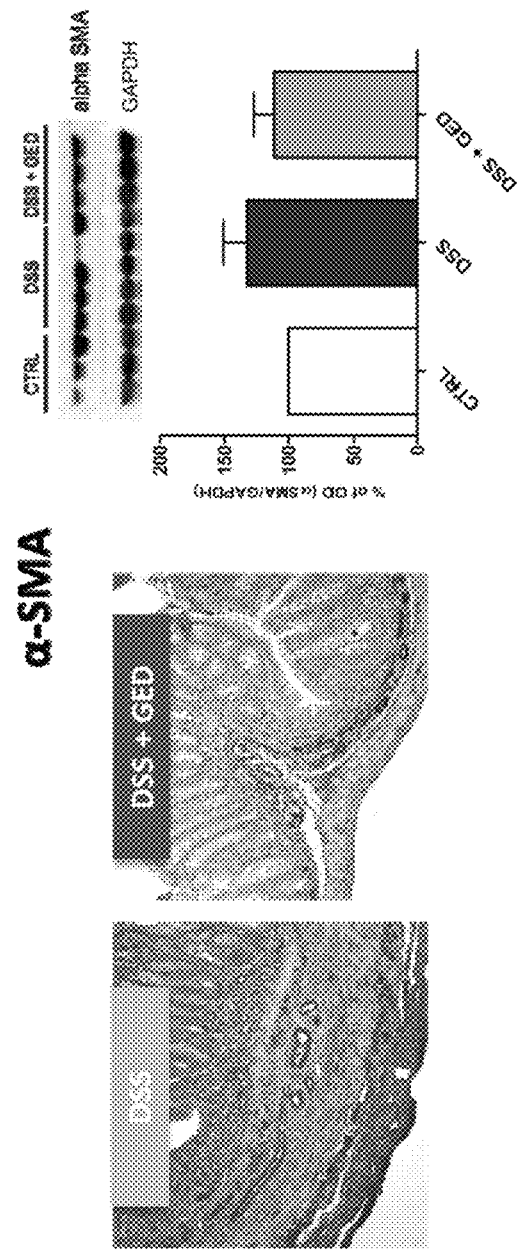
FIGS. 13A and 13B show immunoistochemistry and immunoblotting of the main markers of fibrosis. The microphotograph shows a significant reduction of Collagen I-III (FIG. 13B), α-SMA (FIG. 13A) in DSS mice treated with GED, compared to the mice with DSS-induced chronic colitis. The protein levels of these markers were measured also by Western blotting confirming the expression profile induced by GED. Representative blots are shown. *=$p<0.05$, **=$p<0.01$. N=6 mice for the control group, 8 mice for DSS group, 8 mice for DSS+GED group.
Figure 13B:
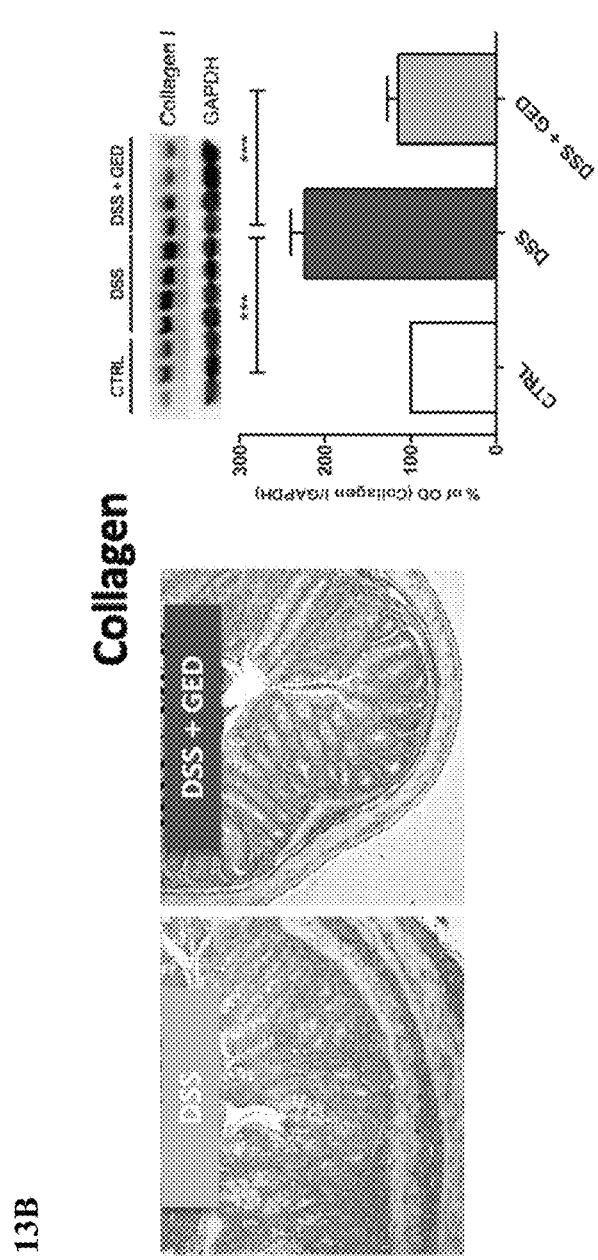

The tissue levels of main markers of fibrosis in the chronic model of DSS-induced colitis were evaluated by immunohistochemical analysis and confirmed by immunoblotting. Thus, a marked reduction of Collagen I-III (FIG. 13B) and α-SMA (FIG. 13A), the specific markers of fibroblasts differentiation, in colons of mice subjected to the oral administration of GED treatment, compared to mice receiving only DSS, was observed. The expression levels of Collagen I-III and α-SMA were measured on 6 control mice, 8 DSS mice and 8 DSS+GED mice. Both immunochemistry and western blotting showed that all of main fibrosis markers were significantly increased in the group of mice receiving the DSS compared to control mice receiving regular water, and that daily administration of GED is associated with their reduced expression. The expression levels of each protein were expressed as percentage of the mean of control group and each marker of interest was normalized with a housekeeping protein like GAPDH. A marked increase of collagen I-III expression (184%) in DSS mice compared with the control group, as well as moderated upregulation of 25% for α-SMA, was observed. The oral administration of GED in mice with DSS-induced chronic colitis caused a reduction in expression levels of these proteins, more significantly marked for Collagen I-III (90.75%±19.9% for GED vs. 284.4%±63.8% for DSS, p<0.005).

GED Controls the TGFβ/Smad Pathway and its Specific Activator, IL13.

The ability of GED to control the TGFβ/Smad pathway at different levels was observed by immunohistochemical analysis and demonstrated a marked reduction of different members involved in this pathway, such as TGF-β1, Smad3, CTGF (data not shown).

Figure 14A:
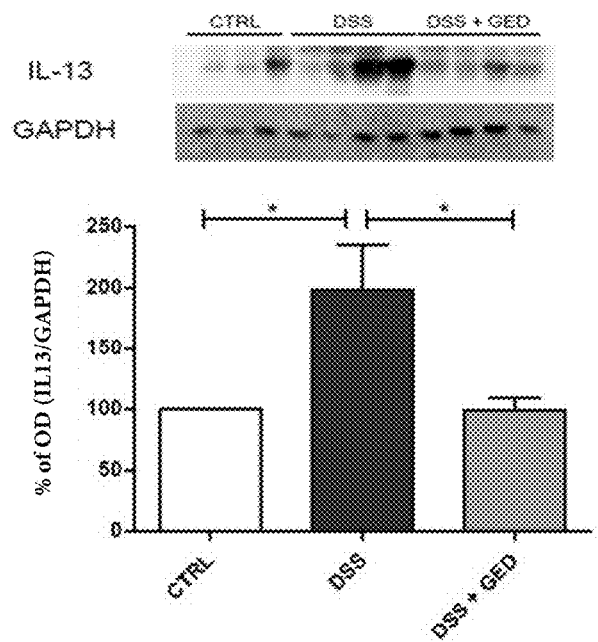
FIGS. 14A, 14B, 14C, 16A, 16B, and 16C show the effect of GED administration on IL-13 protein levels in chronic DSS-treated mice and on its downstream mediators, TGF-β1 and CTGF. IL-13, TGF-β1 and CTGF protein levels were determined by Western blot analysis. Data are presented as percentage of mean controls values. Representative blots are shown. **=$p<0.01$ . . . N=6 mice for the control group, 8 mice for DSS group, 8 mice for DSS+GED group.
Figure 14B:
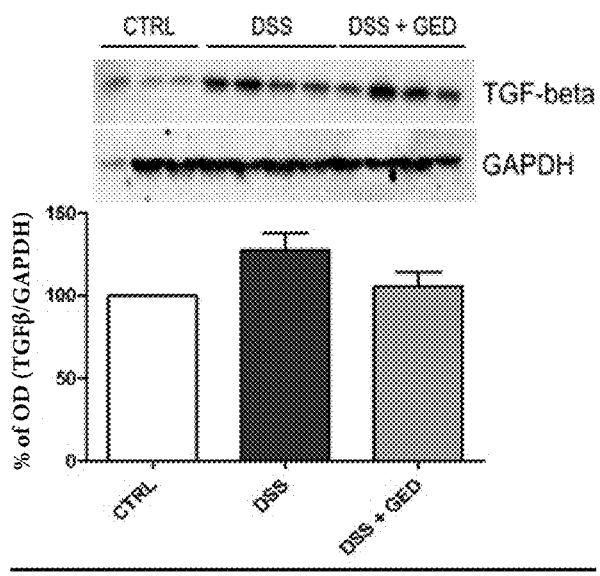
Figure 14C:
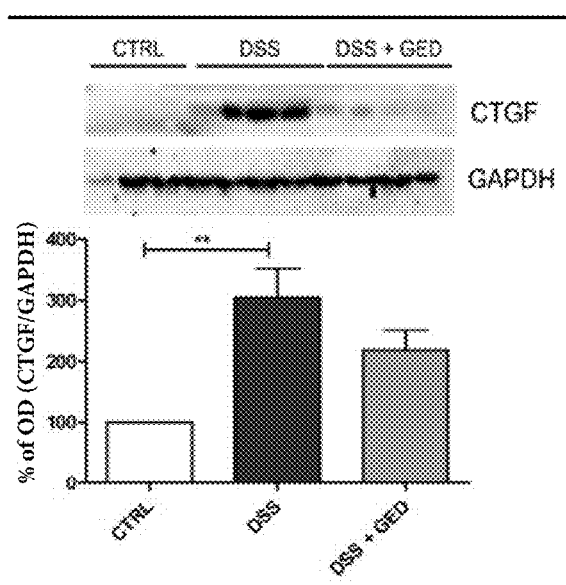
Figure 15:
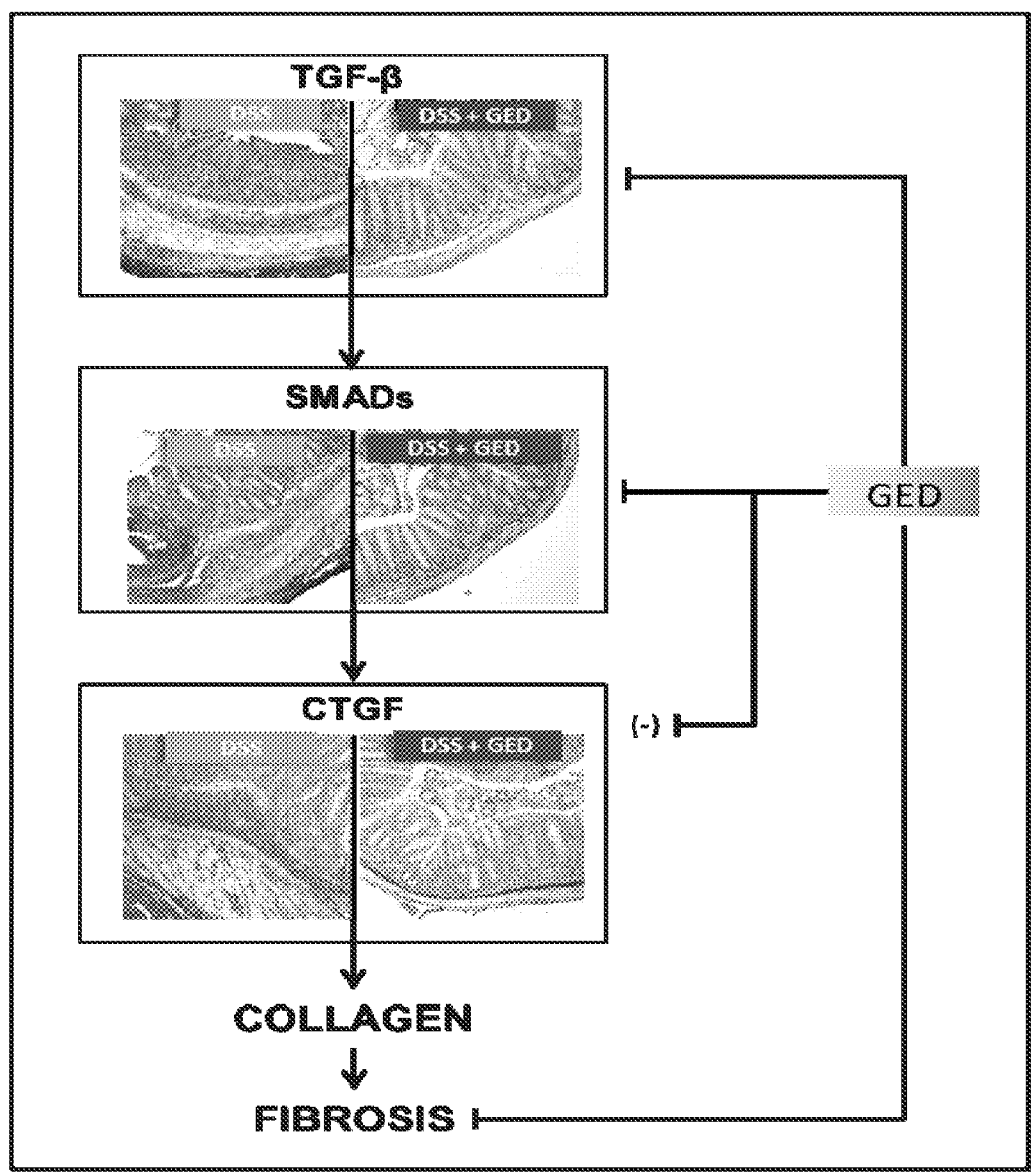
FIG. 15 depicts a microphotograph showing a significant reduction TGF-β1, SMAD 2/3, CTGF in the DSS mice treated with GED, compared to the mice with DSS-induced chronic colitis.
Figure 16A:
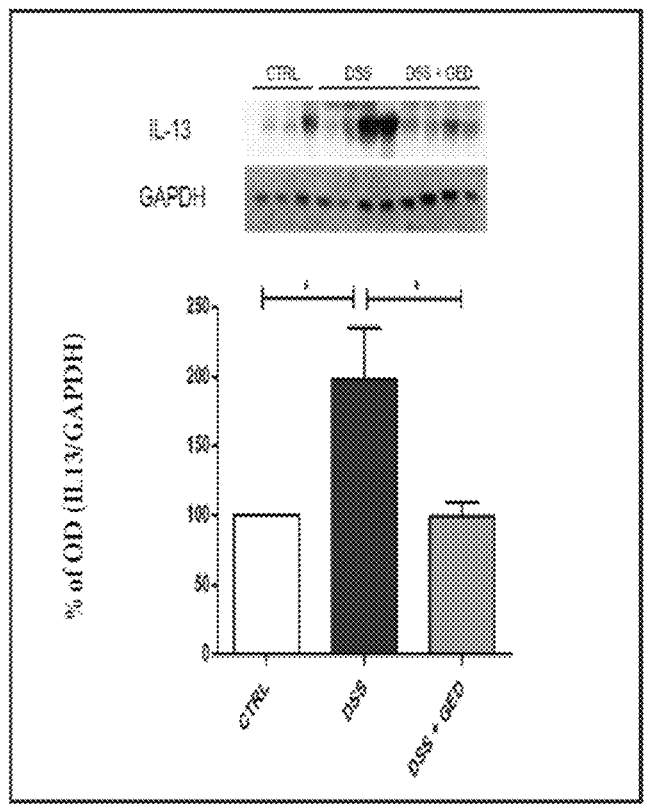
Figure 16B:
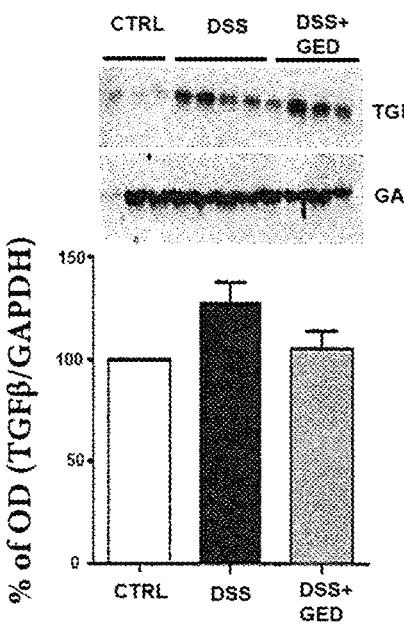
Figure 16C:
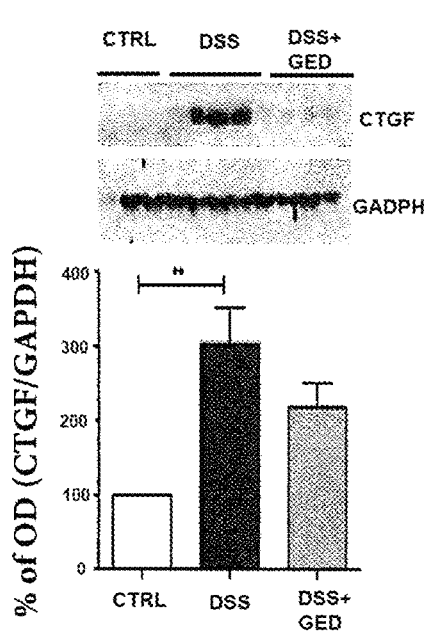

The benefit of GED in the prevention or treatment of intestinal fibrosis relating to variations in IL-13 expression levels was observed FIG. 14A). IL-13 is a specific activator of the TGF β/Smad pathway and this aspect was confirmed by consequent decrease in TGF-β1 (FIG. 14B) and CTGF (FIG. 14C) expression levels. The increased expression of IL-13 in DSS mice was significantly restored by oral administration of GED with 88.88%±14.01% for GED vs. 189.5%±28.71% for DSS, p<0.01. The consequent reduction of expression levels of TGF-β1 and CTGF were confirmed by immunoblotting analysis, with marked significance for CTGF (55.57%±17.53% for GED vs. 115.1%±16.88% for DSS, p<0.05). The expression levels were expressed as percentage of optical density in comparison to control group and normalized with GAPDH.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

We claim:

1. A method of treating hepatic fibrosis, the method comprising administering to a patient in need thereof, a therapeutically effective amount of 2-methoxy-3-(4'-aminophenyl) propionic acid, or a pharmaceutically acceptable salt and/or a stereoisomer thereof.

2. A method of treating hepatic fibrosis, the method comprising administering to a patient in need thereof, a pharmaceutical preparation comprising a therapeutically effective amount of 2-methoxy-3-(4'-aminophenyl) propionic acid, or a pharmaceutically acceptable salt and/or a stereoisomer thereof.

3. The method of claim 2, wherein the pharmaceutical preparation is administered orally.

4. The method of claim 2, wherein the patient is human.

5. The method of claim 2, wherein the 2-methoxy-3-(4'-aminophenyl)propionic acid is (S)-2-methoxy-3-(4'-aminophenyl)propionic acid, or a pharmaceutically acceptable salt thereof.

6. The method of claim 1, wherein the 2-methoxy-3-(4'-aminophenyl)propionic acid is (S)-2-methoxy-3-(4'-aminophenyl)propionic acid, or a pharmaceutically acceptable salt thereof.

7. The method of claim 1, wherein the administering is orally.

8. The method of claim 1, wherein the patient is human.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gggtcagaag gattcctatg                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtctcaaac atgatctggg                                                    20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgggagtaga caaggtacaa ccc                                                23

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catctttctc aaaattcgag tgacaa                                             26

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
```

-continued gatccacact ctccagctgc a          21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caaccaacaa gtgatattct ccatg          25

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagtactgga tcgaccctaa ccaa          24

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acacaggtct gacctgtctc cat          23

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctgacgggc aggtgatc          18

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atgaaagatg gctggaagag agtct          25

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
gcccttcact actgttgac                                                19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acgctgagta cttcgaaat                                                19
```